(12) United States Patent
Bellinger et al.

(10) Patent No.: US 10,849,853 B2
(45) Date of Patent: Dec. 1, 2020

(54) SELF-ASSEMBLED RESIDENCE DEVICES AND RELATED METHODS

(71) Applicants: Massachusetts Institute of Technology, Cambridge, MA (US); The Brigham and Women's Hospital, Inc., Boston, MA (US)

(72) Inventors: Andrew Bellinger, Wellesley, MA (US); Shiyi Zhang, Brookline, MA (US); Carlo Giovanni Traverso, Etobicoke (CA); Robert S. Langer, Newton, MA (US); Stacy Mo, Darien, IL (US); Jiaqi Lin, Somerville, MA (US); Angela DiCiccio, Santa Clara, CA (US); Dean Liang Glettig, Cambridge, MA (US); Lowell L. Wood, Jr., Bellevue, WA (US); Philip A. Eckhoff, Kirkland, WA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/317,628

(22) PCT Filed: Jun. 11, 2015

(86) PCT No.: PCT/US2015/035429
§ 371 (c)(1),
(2) Date: Dec. 9, 2016

(87) PCT Pub. No.: WO2015/191925
PCT Pub. Date: Dec. 17, 2015

(65) Prior Publication Data
US 2017/0135954 A1 May 18, 2017

Related U.S. Application Data

(60) Provisional application No. 62/010,992, filed on Jun. 11, 2014.

(51) Int. Cl.
| | |
|---|---|
| *A61K 9/00* | (2006.01) |
| *A61K 47/58* | (2017.01) |
| *A61K 9/48* | (2006.01) |
| *A61K 47/34* | (2017.01) |
| *C08G 83/00* | (2006.01) |
| *C08G 18/73* | (2006.01) |
| *C08G 63/08* | (2006.01) |
| *C08G 18/42* | (2006.01) |
| *A61K 47/69* | (2017.01) |
| *A61K 31/357* | (2006.01) |
| *A61K 31/65* | (2006.01) |

(Continued)

(52) U.S. Cl.
CPC .......... *A61K 9/0065* (2013.01); *A61K 9/0053* (2013.01); *A61K 9/48* (2013.01); *A61K 31/357* (2013.01); *A61K 31/65* (2013.01); *A61K 31/7048* (2013.01); *A61K 47/10* (2013.01); *A61K 47/32* (2013.01); *A61K 47/34* (2013.01); *A61K 47/40* (2013.01); *A61K 47/42* (2013.01); *A61K 47/58* (2017.08); *A61K 47/6901* (2017.08); *A61M 31/002* (2013.01); *C08G 18/4277* (2013.01); *C08G 18/73* (2013.01); *C08G 63/08* (2013.01); *C08G 83/006* (2013.01); *C08L 33/02* (2013.01); *C08L 33/08* (2013.01); *C08L 33/14* (2013.01); *C08G 2230/00* (2013.01); *C08L 2203/02* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,676,507 | A | 6/1987 | Patterson |
| 5,443,843 | A | 8/1995 | Curatolo et al. |

(Continued)

FOREIGN PATENT DOCUMENTS

| | | | |
|---|---|---|---|
| CN | 103654903 A | * | 3/2014 |
| EP | 0344939 B1 | | 1/1993 |

(Continued)

OTHER PUBLICATIONS

Ren, S., et al., "Noncovalently Connected Micelles Based on a b-Cyclodextrin-Containing Polymer and Adamantane End-Capped Poly(e-caprolactone) via Host—Guest Interactions", J. Polymer Science, 2009, pp. 4267-4278.*

(Continued)

*Primary Examiner* — Michael G. Hartley
*Assistant Examiner* — Lance W Rider
(74) *Attorney, Agent, or Firm* — Wolf, Greenfield & Sacks, P.C.

(57) ABSTRACT

Residence devices as well as their related methods of manufacture and use are generally provided. In some embodiments, a residence device includes a plurality of self-assembling structures that assemble in vivo to form an aggregate structure. Each structure of the plurality of structures includes a first side and a first attachment point that attaches to a second attachment point on another structure of the plurality of structures. The aggregate structure may be sized and shaped to maintain an in vivo position relative to an internal orifice of a subject. The attachment between the first and second attachment points may degrade after a period of time.

21 Claims, 14 Drawing Sheets

(51) Int. Cl.

| | |
|---|---|
| *A61K 31/7048* | (2006.01) |
| *A61K 47/32* | (2006.01) |
| *C08L 33/02* | (2006.01) |
| *C08L 33/08* | (2006.01) |
| *C08L 33/14* | (2006.01) |
| *A61K 47/10* | (2017.01) |
| *A61K 47/40* | (2006.01) |
| *A61K 47/42* | (2017.01) |
| *A61M 31/00* | (2006.01) |

(56) References Cited

U.S. PATENT DOCUMENTS

| | | | |
|---|---|---|---|
| 6,120,803 | A | 9/2000 | Wong et al. |
| 6,339,116 | B1 | 1/2002 | Afzaki-Ardakani et al. |
| 6,488,962 | B1 | 12/2002 | Berner et al. |
| 7,964,196 | B2 * | 6/2011 | de los Rios .......... A61K 9/5184 424/189.1 |
| 10,413,507 | B2 | 9/2019 | Zhang et al. |
| 10,517,819 | B2 | 12/2019 | Bellinger et al. |
| 10,517,820 | B2 | 12/2019 | Bellinger et al. |
| 10,532,027 | B2 | 1/2020 | Bellinger et al. |
| 2003/0021822 | A1 | 1/2003 | Lloyd |
| 2004/0219186 | A1 | 11/2004 | Ayres |
| 2005/0033331 | A1 * | 2/2005 | Burnett .............. A61B 5/14539 606/154 |
| 2007/0048383 | A1 * | 3/2007 | Helmus .............. A61K 9/0019 424/489 |
| 2007/0264307 | A1 | 11/2007 | Chen et al. |
| 2008/0292691 | A1 * | 11/2008 | Lloyd .................. A61K 9/0007 424/451 |
| 2009/0105531 | A1 | 4/2009 | Boyden et al. |
| 2009/0182424 | A1 * | 7/2009 | Marco .................. A61F 5/0036 623/11.11 |
| 2009/0246142 | A1 * | 10/2009 | Bhatia ................ A61K 49/1833 514/1.1 |
| 2010/0168439 | A1 * | 7/2010 | Olson .................... G09B 23/24 548/417 |
| 2010/0256342 | A1 * | 10/2010 | Salemme ................ B82Y 5/00 530/391.1 |
| 2010/0266655 | A1 | 10/2010 | Dadey |
| 2010/0297009 | A1 * | 11/2010 | Olson .................. C07D 401/08 424/9.1 |
| 2011/0305685 | A1 | 12/2011 | Tseng et al. |
| 2013/0045530 | A1 * | 2/2013 | Gracias .............. B81C 1/00007 435/289.1 |
| 2016/0317796 | A1 | 11/2016 | Zhang et al. |
| 2017/0051099 | A1 | 2/2017 | DiCiccio et al. |
| 2017/0106099 | A1 | 4/2017 | Bellinger et al. |
| 2017/0128576 | A1 | 5/2017 | Zhang et al. |
| 2017/0266112 | A1 | 9/2017 | Bellinger et al. |
| 2019/0070107 | A1 | 3/2019 | Bellinger et al. |
| 2019/0070108 | A1 | 3/2019 | Bellinger et al. |
| 2019/0125667 | A1 | 5/2019 | Bellinger et al. |
| 2019/0133936 | A1 | 5/2019 | Bellinger et al. |
| 2019/0175500 | A1 | 6/2019 | Bellinger et al. |
| 2019/0231697 | A1 | 8/2019 | Bellinger et al. |
| 2019/0254966 | A1 | 8/2019 | Bellinger et al. |
| 2019/0262265 | A1 | 8/2019 | Bellinger et al. |
| 2019/0298652 | A1 | 10/2019 | Bellinger et al. |

FOREIGN PATENT DOCUMENTS

| | | |
|---|---|---|
| JP | H03-128934 A | 5/1991 |
| JP | H03-163011 A | 7/1991 |
| JP | 2006-518392 A | 8/2006 |
| WO | WO 2006/084164 A2 | 8/2006 |
| WO | WO 2008/140651 A2 | 11/2008 |
| WO | WO 2009/132461 A1 | 11/2009 |
| WO | WO 2010/099466 A2 | 9/2010 |
| WO | WO 2011/139796 A2 | 11/2011 |
| WO | WO 2014/014348 A1 | 1/2014 |

OTHER PUBLICATIONS

Six-Pentagons, "Six-Pentagons Polylink" accessed from: http://makingmathvisible.com/Polylinks/polylinks-3.html, accessed on Dec. 23, 2017, pp. 1-4.*

Miao, L., et al., "Exploring the Tumor Microenvironment with Nanoparticles" Cancer Treat Res. 2015, pp. 193-226 (Year: 2015).*

CN103654903A translation, accessed from https://patents.google.com/patent/CN103654903A/en?oq=CN103654903A, accessed on Oct. 29, 2018, pp. 1-4 (Year: 2018).*

Ethicon, "Wound Closure Manual", Ethicon a Johnson and Johnson company, pp. 1-119 (Year: 2005).*

Neto-Ferreira, R., et al., "Pleiotropic effects of rosuvastatin on the glucose metabolism and the subcutaneous and visceral adipose tissue behavior in C57Bl/6 mice" Diabetology and Metabolic Syndrome, pp. 1-10 (Year: 2013).*

International Search Report and Written Opinion for PCT/US2015/035429 dated Sep. 15, 2015.

International Preliminary Report on Patentability for PCT/US2015/035429 dated Dec. 22, 2016.

Agrawal et al., Clinical relevance of the nutcracker esophagus: suggested revision of criteria for diagnosis. J Clin Gastroenterol. Jul. 2006;40(6):504-9.

Cargill et al., Controlled gastric emptying. 1. Effects of physical properties on gastric residence times of nondisintegrating geometric shapes in beagle dogs. Pharm Res. Aug. 1988;5(8):533-6.

Cargill et al., Controlled gastric emptying. II. In vitro erosion and gastric residence times of an erodible device in beagle dogs. Pharm Res. Jun. 1989;6(6):506-9.

Choudhry et al. Full coverage for preventive medications after myocardial infarction. N Engl J Med. Dec. 1, 2011;365:2088-97. doi: 10.1056/NEJMsa1107913. Epub Nov. 14, 2011.

Davies et al., Release characteristics, ovarian activity and menstrual bleeding pattern with a single contraceptive implant releasing 3-ketodesogestrel. Contraception. Mar. 1993;47(3):251-61.

Farra et al., First-in-human testing of a wirelessly controlled drug delivery microchip. Sci Transl Med. Feb. 22, 2012;4(122):122ra21, 12 pages. doi: 10.1126/scitranslmed.3003276. Epub Feb. 16, 2012.

Mintchev et al., Pilot study of temporary controllable gastric pseudobezoars for dynamic non-invasive gastric volume reduction. Physiol Meas. Feb. 2010;31(2):131-44. doi: 10.1088/0967-3334/31/2/001. Epub Dec. 11, 2009.

Olson et al., Chemical mimicry of viral capsid self-assembly. Proc Natl Acad Sci U S A. Dec. 26, 2007;104(52):20731-6. Epub Dec. 18, 2007.

Osterberg et al., Adherence to medication. N Engl J Med. Aug. 4, 2005;353(5):487-97.

Phillips et al., Gastric trichobezoar: Case report and literature review. Mayo Clin Proc. Jul. 1998;73(7):653-6. Review.

Richter et al., Esophageal manometry in 95 healthy adult volunteers. Variability of pressures with age and frequency of "abnormal" contractions. Dig Dis Sci. Jun. 1987;32(6):583-92.

Salunke et al., Self-assembly of purified polyomavirus capsid protein VP1. Cell. Sep. 12, 1986;46(6):895-904.

Singer et al., The fluid mosaic model of the structure of cell membranes. Science. Feb. 18, 1972;175(4023):720-31.

Singh et al., Floating drug delivery systems: an approach to oral controlled drug delivery via gastric retention. J Control Release. Feb. 3, 2000;63(3):235-59.

Timmer et al., Pharmacokinetics of etonogestrel and ethinylestradiol released from a combined contraceptive vaginal ring. Clin Pharmacokinet. Sep. 2000;39(3):233-42.

Whitesides et al., Self-assembly at all scales. Science. Mar. 29, 2002;295(5564):2418-21.

Wilber et al., Self-assembly of monodisperse clusters: Dependence on target geometry. J Chem Phys. Nov. 7, 2009;131(17):175101(1-13). doi: 10.1063/1.3243580.

Wilber et al., Monodisperse self-assembly in a model with protein-like interactions. J Chem Phys. Nov. 7, 2009;131(17):175102(1-10). doi: 10.1063/1.3243581.

U.S. Appl. No. 15/307,806, filed Oct. 28, 2016, DiCiccio et al.

U.S. Appl. No. 15/317,566, filed Dec. 9, 2016, Bellinger et al.

(56) References Cited

OTHER PUBLICATIONS

U.S. Appl. No. 15/143,230, filed Apr. 29, 2016, Zhang et al.
U.S. Appl. No. 15/317,601, filed Dec. 9, 2016, Zhang et al.
PCT/US2015/035429, Sep. 15, 2015, International Search Report and Written Opinion.
PCT/US2015/035429, Dec. 22, 2016, International Preliminary Report on Patentability.
U.S. Appl. No. 16/014,549, filed Jun. 21, 2018, Bellinger et al.
EP 15805932.9, Dec. 20, 2017, Extended European Search Report.
Extended European Search Report dated Dec. 20, 2017 for Application No. EP 15805932.9.
Uhrich et al., Polymeric Systems for Controlled Drug Release. Chem Rev. 1999;99:3181-98.

* cited by examiner

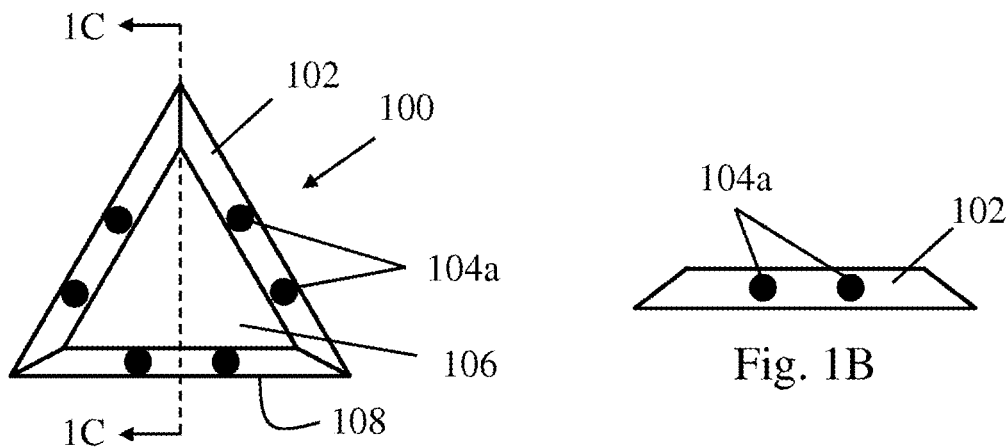
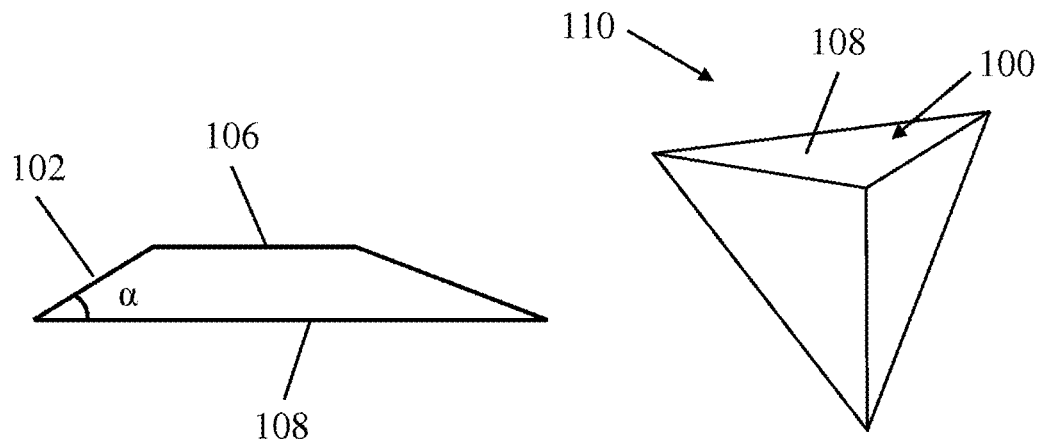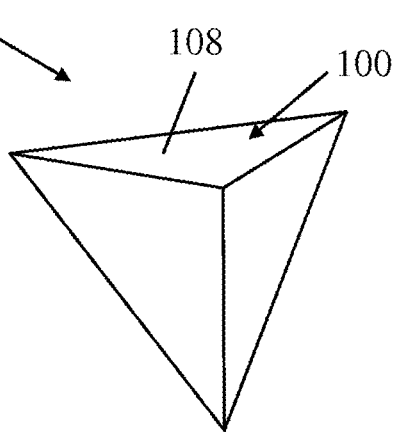
Fig. 1A
Fig. 1B
Fig. 1C
Fig. 1D

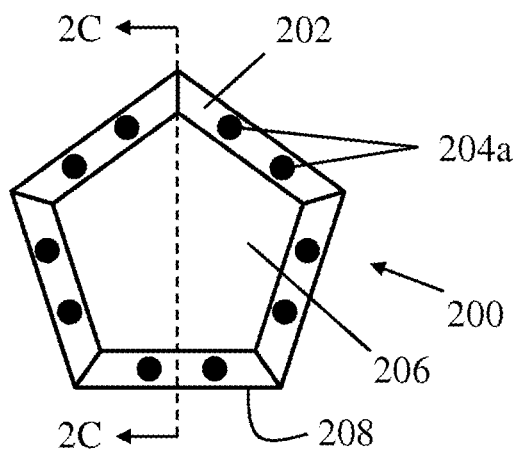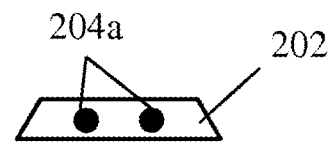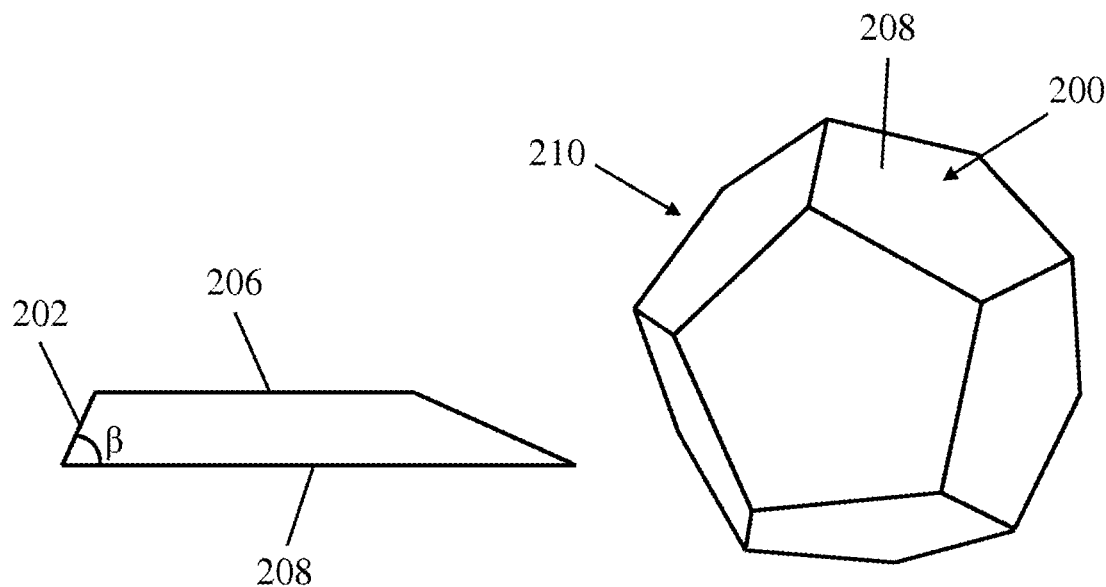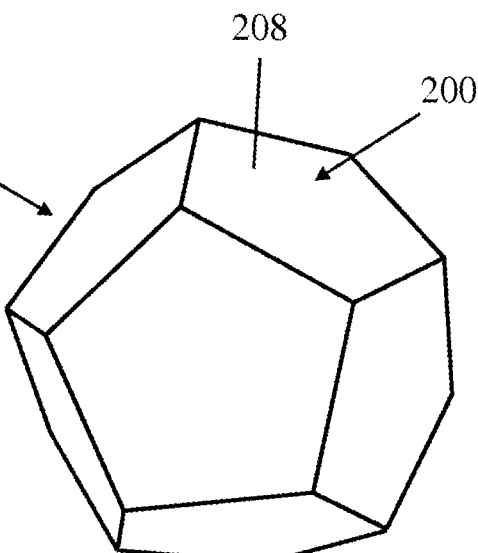
Fig. 2A  Fig. 2B
Fig. 2C  Fig. 2D

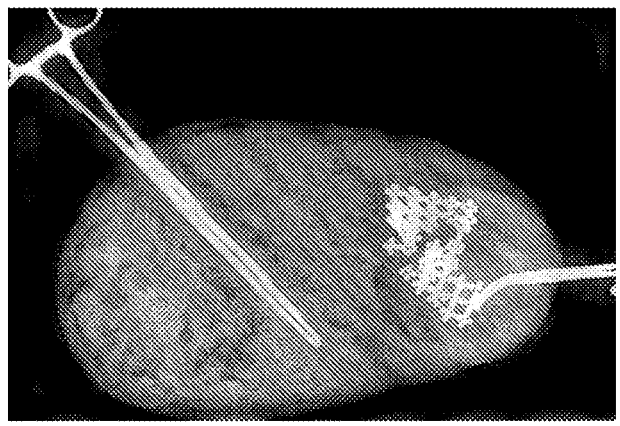
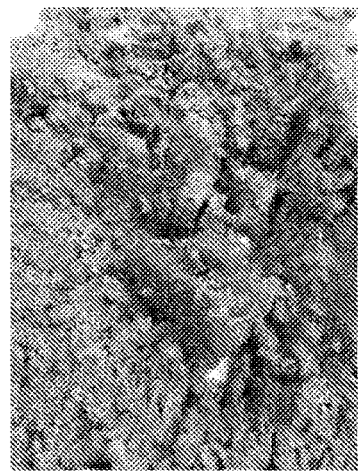
Fig. 10A (Day 0)
Fig. 10B (Day 1)
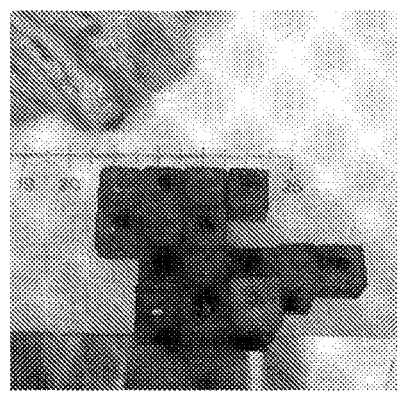
Fig. 10C
Fig. 10D
Fig. 10E

SELF-ASSEMBLED RESIDENCE DEVICES AND RELATED METHODS

RELATED APPLICATIONS

This application is a national stage application under 35 U.S.C. § 371 of International Patent Application Serial No. PCT/US2015/035429, filed on Jun. 11, 2015, entitled "SELF-ASSEMBLED RESIDENCE DEVICES AND RELATED METHODS," which claims priority under 35 U.S.C. § 119(e) to U.S. Provisional Application Ser. No. 62/010,992, filed Jun. 11, 2014, the contents of which are incorporated herein by reference in their entirety for all purposes.

STATEMENT OF GOVERNMENT SUPPORT

This invention was made with Government support under Grant No. R37 EB000244 awarded by the National Institutes of Health. The Government has certain rights in the invention.

FIELD

Disclosed embodiments are related to self-assembled residence devices and related methods.

BACKGROUND

Adherence of patients to self-administered therapeutics and diagnostics regimes over an extended or indefinite duration is often poor, with adherence rates to oral therapies for chronic asymptomatic conditions estimated to be less than 50%. The challenge of low adherence is greatest in primary and secondary prevention applications where a disease to be prevented or treated is often asymptomatic and the therapy has no immediate tangible benefit. Many factors contribute to low adherence including cost, access, side effects, and the inconvenience of dosing regimens.

Current state-of-the-art approaches to adherence include educational interventions, telephone-based counseling, health information technology solutions, interactive pharmacy tools, and changing models of payment for care, such as no-copayment plans after myocardial infarction. All of these approaches have achieved only modest improvements. Meanwhile, pharmacologic solutions to the adherence problem are limited to invasive delivery devices and a subset of pharmacologic agents formulated for extended release. Recent advances in extended release pharmacologic systems are predominantly limited to subcutaneous, transdermal, intravaginal, and surgical implants. Demonstrated solutions include invasive modalities such as surgical implants (including, e.g., wireless, programmable devices available from MicroCHIPS, Inc. (Lexington, Mass.)) or modalities limited to specialized applications such as birth control (including, e.g., NuvaRing® and Implanon®, both available from Merck & Co., Inc. (Whitehouse Station, N.J.)). Devices like MicoCHIPS are also limited to delivering therapeutic agents with high potency because they can be administered in only microgram or smaller quantities.

Oral administration has the potential for the widest patient acceptance. However, no oral delivery system has been demonstrated to enable extended release via the oral route due to a number of fundamental barriers. Principally, the transit time for a bolus of food through, for example, the human gastrointestinal tract is rapid, typically lasting about 24 to 48 hours. This residence time includes about 1 to 2 hours in the stomach, about 3 hours in the small intestine, and about 6 to 12 hours in the large intestine. One strategy for extended duration therapeutic delivery, therefore, would be to prolong the transit time of an orally-administered therapeutic (but not food). Gastric residence and/or slowed transit could be attempted and/or tolerated at a number of segments of a gastrointestinal tract, as evidenced by bezoars and bariatric devices. Bezoars (i.e., masses found trapped in the gastrointestinal system) can form from a variety of materials that are indigestible (such as food aggregates and hair) and often become clinically apparent in adult humans only at sizes in the hundreds of grams. A bariatric device, such as an endoscopically-administered intra-gastric balloon, can be used to fill a portion of a patient's stomach to achieve noninvasive gastric reduction for weight loss. Previous attempts at gastric residence for drug delivery include mucoadhesion, gastric swelling, and flotation on gastric fluids. However, none of these approaches have demonstrated gastric residence for more than 24 hours, let alone progressed to clinical use

SUMMARY

In one embodiment, a residence device includes a plurality of self-assembling structures. Each structure of the plurality of structures includes a first attachment point on the first side. The first attachment point attaches to a second attachment point on another structure of the plurality of structures. The attachment between the first attachment point and the second attachment point degrades after a period of time when the plurality of structures are placed in vivo.

In another embodiment, a residence device includes a plurality of self-assembling structures. Each structure of the plurality of structures includes a first attachment point on the first side. The first attachment point attaches to a second attachment point on another structure of the plurality of structures. The plurality of structures are sized and shaped to form an aggregate structure in vivo, and the aggregate structure is sized and shaped to maintain an in vivo position of the aggregate structure relative to an internal orifice.

In yet another embodiment, a method of administering a residence device includes administering, to a subject, a plurality of self-assembling structures. Each structure of the plurality of structures has a first side with a first attachment point for attaching to a second attachment point on another structure of the plurality of structures. The method further includes degrading the attachment between the first attachment point and the second attachment point after a period of time.

In a further embodiment, a method of administering a residence device includes administering, to a subject, a plurality of self-assembling structures. Each structure of the plurality of structures has a first side with a first attachment point for attaching to a second attachment point on another structure of the plurality of structures. The method further includes forming an aggregate structure in vivo. The aggregate structure is sized and shaped to maintain an in vivo position of the aggregate structure relative to an internal orifice.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 1A is a schematic representation of one embodiment of a self-assembling structure configured to form a tetrahedral aggregate structure;

FIG. 1B is a schematic representation of one side of the self-assembling structure of FIG. 1A;

FIG. 1C is a cross-sectional view of the self-assembling structure of FIG. 1A;

FIG. 1D is a perspective view of a tetrahedral aggregate structure formed from four of the self-assembling structures of FIG. 1A;

FIG. 2A is a schematic representation of one embodiment of a self-assembling structure configured to form a dodecahedral aggregate structure;

FIG. 2B is a schematic representation of one side of the self-assembling structure of FIG. 2A;

FIG. 2C is a cross-sectional view of the self-assembling structure of FIG. 2A;

FIG. 2D is a perspective view of a dodecahedral aggregate structure formed from twelve of the self-assembling structures of FIG. 2A;

FIGS. 10A-10E show semi-ordered structures retained in a gastric cavity as examined during a necropsy;

DETAILED DESCRIPTION

Figure 3A:
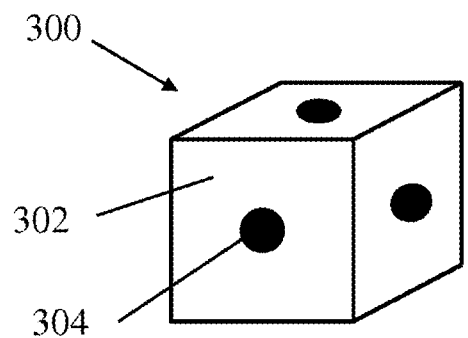
FIG. 3A is a schematic representation of one embodiment of a self-assembling structure configured to form a semi-ordered aggregate structure.

Residence devices, and related methods are generally described. Certain embodiments comprise administering (e.g., orally) a residence device to a subject (e.g., a patient) such that the residence device is retained at a location internal to the subject for a particular amount of time (e.g., at least about 24 hours) before being released. The residence device may be, in some cases, a gastric residence device. In some embodiments, the devices and systems described herein comprise one or more materials configured for high levels of active substances (e.g., a therapeutic agent) loading, high active substance and/or device stability in acidic environments, mechanical flexibility and strength in an internal orifice (e.g., gastric cavity), easy passage through the GI tract until delivery to at a desired internal orifice (e.g., gastric cavity), and/or rapid dissolution/degradation in a physiological environment (e.g., intestinal environment) and/or in response to a chemical stimulant (e.g., ingestion of a solution that induces rapid dissolution/degradation). In certain embodiments, the device includes one or more materials capable of controlled release of therapeutic, diagnostic, and/or enhancement agents as well as structural materials necessary for gastric residence but capable of controlled and/or tunable degradation/dissolution to determine the time at which retention shape integrity is lost and the device passes out of the gastric cavity. For example, in certain embodiments, the residence device comprises a plurality of self-assembling structures configured to form an aggregate structure in vivo. In some embodiments, the aggregate structure may be configured to release an active substance (e.g., a therapeutic agent). Further, in some such embodiments, the aggregate structure may be configured to degrade such that the residence device breaks apart and is released from an internal location of the subject after a predetermined amount of time.

Certain of the devices, and methods described herein may be useful, for example, in achieving gastric residence and/or slowed transit via oral administration for extended in vivo residence and administration of therapeutic, diagnostic, and/or enhancement agents. The devices described herein may offer several advantages as compared to traditional residence and/or orally administered devices and systems including, for example, the ability to adopt a shape and/or size small enough to be ingested by a subject; adopt a shape and/or size that slows or prevents further transit in the gastric cavity (e.g., passage from the body of the stomach through the pylorus); high load levels (e.g., high mass) of therapeutic, diagnostic, and/or enhancement agents; controlled release of therapeutic, diagnostic, and/or enhancement agents with low to no potential for burst release; maintain stability of therapeutic, diagnostic, and/or enhancement agents in a hostile environment, such as the gastric environment, for an extended duration; maintain safety with low to no potential for gastric or intestinal obstruction and/or perforation; and/or degrade, dissolve, and/or disassociate into one or more forms capable of passing through a gastrointestinal tract. In certain embodiments, the devices and systems described herein may be configured with durable residence times greater than at least twenty-four hours and lasting up to about one year, or more. In some embodiments, the systems, devices, and methods described herein are compatible with subjects, including, but not limited to humans and non-human animals. In further embodiments, the systems and devices can be configured to deliver a wide variety of therapeutic, diagnostic, and/or enhancement agents, thus potentially increasing and even maximizing adherence rates.

According to one aspect of the present disclosure, a residence device may be formed from a plurality of structures that self-assemble in vivo. For example, in some embodiments, each structure may include one or more attachment points on sides of the structures that attach to attachment points on other structures of the plurality of structures. In this manner, the individual structures attach to one another to form a residence device in the form of an aggregate structure that is sized, shaped, and sufficiently strong and/or stable to maintain an in vivo position relative to an internal orifice. In some embodiments, the attachment between the attachment points of the self-assembling structures may degrade after a period of time (e.g., a retention or residence time period) such that the aggregate structure disassembles. After disassembly, the individual structures may be sized such that they pass through the internal orifice.

As noted above, a residence device may maintain an internal position within a subject for a residence time period, after which the attachments may degrade. The term residence time period generally refers to the length of time during which a residence device as described herein resides at an internal location of a subject. This time period may be measured from the time the residence device is initially present in the internal location of the subject to the time when the device is no longer present at the internal location due to, for example, degradation, dissolution, and/or exit of at least a portion of the device from the internal location of the subject. In an illustrative embodiment, the device may be orally administered such that the device resides at an internal location of the subject for a period of time prior to passing through an internal orifice. For example, in one such embodiment, the residence device enters the stomach above the pylorus and exits through the pylorus into the intestine (e.g., after degradation of at least a portion of the device). In such an embodiment, the residence time period is measured as the length of time between when the device initially resides in the stomach and when the device exits through the pylorus.

In some embodiments, the residence time period of a residence device is greater than or equal to about 24 hours, 48 hours, 3 days, 7 days, 1 month, 6 months, 1 year, or any other desired time period. Correspondingly, the residence time period is less than or equal to about 2 years, 1 year, 6 months, 1 month, 7 days, 3 days, 48 hours, or any other desired time period. Combinations of the above-referenced ranges are also possible (e.g., between about 24 hours and 2 years, between about 24 hours and 1 year, between about 48 hours and 7 days, between about 3 days and 1 month, between about 7 days and 6 months, between about 1 month and 1 year). Other ranges are also contemplated.

In some embodiments, a plurality of self-assembling structures may form an ordered aggregate structure. For example, the self-assembling structures may be configured to assemble into at least a portion of a polyhedron such as a tetrahedron, cube, octahedron, dodecahedron, or an icosahedron. It should be understood that any other suitable shape or structure, including other polyhedral structures, may also be suitable, as the present disclosure is not limited in this manner. In some embodiments, a polyhedral aggregate structure is a platonic solid.

In certain embodiments, a polyhedral aggregate structure may have a hollow interior. In such an embodiment, the self-assembling structures may be plate-like structures having a polygonal shape such that the structures form surfaces of the polyhedron. For example, a tetrahedral aggregate structure may be formed from four triangular structures, a cube may be formed form six square structures, an octahedron may be formed from eight triangular structures, a dodecahedron may be formed from twelve pentagonal structures or an icosahedron may be formed from twenty triangular structures though other possible structures are also contemplated. Moreover, in some embodiments, different self-assembling structures may have different sizes and/or shapes and may not form shapes that are regular polygons, as the disclosure is not so limited. In such an embodiment, these structures may not assemble to form a regular polyhedral structure. Consequently, a polyhedral aggregate structure may include any suitable number of polygonal self-assembling structures that are attached to form any portion of a polyhedral structure.

In some embodiments, including embodiments where plate like structures are used, polygonal self-assembling structures may attach along their respective sides to form a polyhedral aggregate structure. For example, in some embodiments, each polygonal structure may have an exterior surface that surfaces outwards when assembled in an aggregate structure, an opposing interior surface that surfaces inwards when assembled in an aggregate structure, and one or more sides extending between the exterior and interior surfaces. One or more discrete attachment points are positioned either on, or in, the sides in a manner to facilitate attaching to corresponding attachment points on other polygonal structures. Depending on the particular embodiment, a side may have any appropriate number of attachment points including zero, one, two, three, or more attachment points. Additionally, different sides on a single self-assembling structure may have different numbers of attachment points. In some embodiments, the attachment points may be generally centered on the side, or in other embodiments, the attachment points may be positioned closer to the edges, uniformly distributed along the length of a side, or randomly distributed along a side as the disclosure is not limited to any particular arrangement of the attachment points. The different sides of a self-assembling structure may also have the attachment points arranged in either the same or in different ways relative to each other. Furthermore, in some embodiments, attachment points may not be discrete points, and may instead be distributed along a portion, or the entirety, of a side. For example, in one embodiment, an entire side of a structure may correspond to an attachment point. In view of the above, it should be understood that a side may have any suitable number of attachment points, and that the attachment points may be arranged in any suitable manner on the side.

Depending on the particular embodiment, self-assembly of a plurality of structures may be governed by the interactions of two or more components located at the attachment points on the structures. For example, the components may include complementary elements which interact to form an attachment between adjacent structures. In some embodiments, the attachment points may include magnets arranged such that the north or south pole of the magnet is positioned at the surface of the structure at the attachment point. In such embodiments, a north pole of a magnet at one attachment point on one structure may interact with a south pole of a magnet at an attachment point on another structure. In some embodiments, multiple magnets having the same, or different magnetic orientations, may be positioned on a single side of a structure to form multiple attachment points. Alternatively, in some embodiments, the attachment between structures may be formed using chemical interactions rather than magnetic interactions. In one such embodiment, the attachment points may include protein/ligand complexes. For instance, a first attachment point may comprise biotin and a second attachment point may comprise streptavidin which will bond to one another when the corresponding portions of the different attachment points are approximated next to one another in vivo. In yet another embodiment, a guest/host complex, such as a adamantine-cyclodextrine complex, is used to form the attachment between two structures. In view of the above, it should be understood that any suitable interaction between two attachment points capable of bonding two structures together in vivo may be used to control the self-assembly of a plurality of self-assembling structures as the disclosure is not limited in this manner.

In some embodiments, one or more self-assembling structures have a circumscribing radius between, for example, 0.6 cm and 1.7 cm, and a volume between, for example 300 mm$^3$ and 1,300 mm$^3$. However, it should be understood that structures with different sizes and circumscribing radii may also be suitable, as the disclosure is not so limited.

In some embodiments, an aggregate structure has a compressive strength which is generally greater than or about equal to the maximum pressure that the aggregate structure may experience in an in vivo environment. For example, in one embodiment, a dodecahedral structure, or other structure, has a compressive strength of about 5N, which is comparable to estimates of the maximum pressure exerted at the human gastro-esophageal sphincter. However, it should be understood that in some embodiments, an aggregate structure may have a strength that is greater than 5N or less than 5N. For example, an aggregate structure may have a compressive strength between about 4N and 6N, 5N and 10N, or any other range of forces as the disclosure is not so limited.

According to some embodiments, a residence device may be administered to a subject by administering a plurality of self-assembling structures. The structures may be configured to form an ordered structure such as a polyhedron or a semi-ordered structure, as discussed herein. The plurality of structures may self-assemble in vivo by a stochastic process where attachment points of different structures are approximated to one another forming an attachment there between. As the attachment process between individual structures continue, larger resulting aggregate structures are formed. The final resulting one or more aggregate structures may have a size and/or shape that maintain an in vivo position of the aggregate structures relative to an internal orifice. In some embodiments, the residence device may release an active substance while maintained at the internal position, as described in more detail below. After a period of time (e.g., the residence time), the aggregate structure may disassemble, for example, through degradation of attachments between attachment points on the self-assembling structures, as discussed above. Alternatively, in some embodiments, the aggregate structure may not undergo degradation until a material that actively degrades the attachments and/or self-assembling structures is introduced into the in vivo environment. For example, as detailed further below, an alkaline material such as sodium bicarbonate might be ingested to alter the pH of the gastric environment to induce the rapid degradation of the aggregate structure. After the aggregate structure is sufficiently degraded, it may disassemble into smaller fragments, and/or individual structures, that are capable of passing through the internal orifice.

In order to facilitate the formation of aggregate structures, in some embodiments, the sides of a polygonal self-assembling structure may be oriented at an angle relative to the exterior or interior surface of a structure. Such an angle may define a dihedral angle formed by the structures when they assemble to form a portion of an aggregate polyhedron structure. Specifically, the interior angle formed between a side and the exterior surface of a self-assembling structure may define half of the dihedral angle, such that when two structures attach along their sides, the interior and exterior surfaces of the respective structures are oriented at the natural dihedral angle of the polyhedron. The specific angle may be chosen such that the polygonal structure forms a desired polyhedron. For example, triangular self-assembling structures that have sides oriented at different angles to facilitate assembly into tetrahedral, octahedral, or icosahedral structures.

In some embodiments, a side may be angled such that an assembled polyhedron has surfaces oriented at its natural dihedral angle to form an exact geometric fit. For example, in one embodiment, pentagonal structures configured to form a dodecahedron may include sides oriented at an angle of about 58.3° with respect to the exterior surface such that the dihedral angle formed by surfaces of the assembled dodecahedron is about 116.6°. Alternatively, the sides may be oriented such that the resulting polyhedron features a dihedral angle which does not correspond to an exact geometric fit between adjacent surfaces. For example, in some embodiments, pentagonal structures configured to form a dodecahedron may have sides oriented at an angle between about 58.3° and about 66°, or between about 62° and 63.5° with respect to the exterior surface such that the resulting dihedral angle is between about 116.6° and 132°, or between about 124° and 127°, respectively. In some embodiments, all of the sides on a single polygonal self-assembling structure may form the same angle with respect to the exterior surface. Alternatively, different sides may form different angles such that an assembled polyhedron features a variable dihedral angle. Further, while specific angles have been given above for a particular geometry, it should be understood that any appropriate angle may be used with any desired geometry. For example, in one embodiment, a side may be angled such that the resulting dihedral angle is between about 5° and 10° larger or smaller than the natural dihedral angle of the resulting polyhedral structure.

Turning now to the figures, several non-limiting embodiments are described in more detail. It should be understood that the various components, features, and methods described with regards to the figures may be combined in any desirable manner as the disclosure is not limited to only those specific embodiments described and depicted herein.

One exemplary embodiment of a self-assembling polygonal structure is depicted in FIGS. 1A-1D. In the depicted embodiment, the self-assembling structures 100 have triangular plate like shapes including three sides 102 extending between an interior surface 106 and an exterior surface 108. Two or more attachment points 104a are generally centered on the sides. However, as described above, the sides may have any suitable number of attachment points arranged in any suitable manner. FIG. 1C is a cross-sectional view of the structure, and illustrates that the sides forms an interior angle α with respect to the exterior surface 108. Depending on the particular value of α, the triangular structures may assemble into a tetrahedron, an octahedron, an icosahedron, or any other suitable structure. FIG. 1D depicts one example of an aggregate tetrahedral structure 110 formed from four assembled triangular structures 100. The exterior surfaces 108 of the triangular structures form the exterior surfaces of the tetrahedron.

FIGS. 2A-2D depict another exemplary embodiment of a self-assembling structure similar to the above triangular structures and resulting tetrahedron aggregate. In this embodiment, the self-assembling structures 200 have pentagonal plate like shapes including five sides 202 extending between an interior surface 206 and an exterior surface 208. Similar to the above-described embodiment, the sides 202 include two attachment points 204a. The sides are also oriented at an angle β with respect to the exterior surface 208 such that the pentagonal structures assemble to form a dodecahedral structure 210, as depicted in FIG. 2D. As described above, the angle β may be chosen such that the dihedral angles of the dodecahedron may, or may not equal the natural dihedral angle corresponding to an exact geometric fit.

As noted above, in some embodiments, a plurality of self-assembling structures may not form an ordered aggregate structure such as a polyhedron. Instead, the self-assembling structures may attach in a "semi-ordered" arrangement such that it does not have a defined shape. For example, in one embodiment, self-assembling structures may be formed as polyhedrons, such as cubes, that include attachment points on at least three surfaces of the polyhedron. In such an embodiment, it may be desirable for the polyhedrons to attach to one another in any orientation. Therefore, in some embodiments, the attachment points are not selective relative to one another.

Figure 3B:
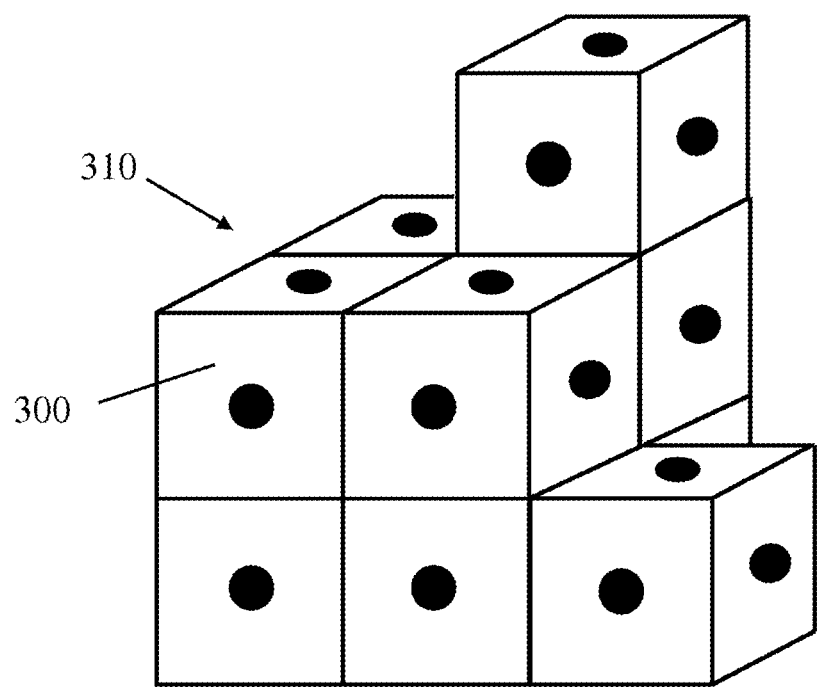
FIG. 3B is a schematic representation of a semi-ordered aggregate structure formed from eight of the self-assembling structures of FIG. 3A.

FIGS. 3A-3B depict a schematic representation of one exemplary embodiment of a self-assembling polyhedron corresponding to cubes 300 which form a semi-ordered aggregate structure 310. The cubes include six surfaces 302, and attachment points 304 are provided on at least three of those surfaces. In the depicted embodiment, the cubes include attachment surfaces on each of the six surfaces. When administered, the plurality of cubes, or other structures, are ingested, or otherwise administered to a subject. Once in vivo, the attachment points of different cubes are approximated next to one another in a random stochastic process resulting in bonding of the approximated attachment points. This process continues bonding larger and larger aggregate structures to one another until to form a final aggregate structure that is large enough to avoid passage through a desired orifice in the body. The ordered structures formed from plate like polygonal shapes described above undergo a similar process when administered to a subject and assembled in vivo.

Although cubes are described in the above embodiment, it should be understood that other shapes are also contemplated. For example, self-assembling structures may be formed as spheres, rectangular prisms, tetrahedrons, octahedrons, or any other three dimensional shape, as the disclosure is not so limited. Moreover, the self-assembling structures may include attachment points arranged in any suitable configuration. For example, in the depicted embodiment, at least three attachment points 304 are positioned on surfaces 302 that are mutually orthogonal to one another. In another embodiment, a structure may include at least two, three, or any number of attachment points located on different surfaces of a structure with normal directions that are non-parallel, or otherwise misaligned, with one another. For instance, attachment points may be positioned on the surfaces of a tetrahedron which includes four separate surfaces with four different non-parallel normal directions that are also not orthogonal to one another. Furthermore, although a densely packed aggregate structure 310 is depicted in FIG. 3B, the structures could assemble into any three-dimensional arrangement, which may, or may not, include voids or other open spaces, and may be substantially non-symmetric.

In some embodiments, the attachments formed between adjacent attachment points may degrade after a period of time in vivo. Degradation of the attachments may cause the aggregate structures to disassemble. As the degradation process continues, the resulting disassembled structures may have a size and/or shape small enough to pass through an internal orifice such that the residence device is no longer able to maintain an internal position in a subject. In certain embodiments, the self-assembling structures may be made from a material that swells over a period of time when placed in an in vivo environment. In other embodiments, degradation of the attachments may be caused from biodegradation of chemical attachments, such as protein/ligand or guest/host complexes. Alternatively, the self-assembling structures themselves may degrade over time in an in vivo environment such that the aggregate structure loses structural stability. In such an embodiment, as the self-assembling structures degrade, the aggregate structure may begin to disassemble. In view of the above, it should be understood that a residence device formed from an assembled aggregate structure may disassemble in vivo in any suitable manner using any suitable mechanism as the disclosure is not so limited.

As noted above, in some embodiments, the attachments are selected to control the timing of disassembly of a residence device after the delivery of an active substance for a desired residence time period. For example, in some embodiments, the attachments may sufficiently degrade to disassemble an aggregate structure after about 24 hours, 48 hours, one week, one month, or any other desired time period. After disassembly of the aggregate structure, the resulting fragments, or individual structures, are sufficiently small in size and shape to safely pass through an internal orifice of the gastric cavity and into the lower intestinal tract of a subject. Again, degradation of the attachments may be achieved using biodegradation, swelling of the self-assembling structures, or any other appropriate mechanism such that the ability of the residence device to resist passage through an internal orifice, such as the pylorus, is reduced over time.

Figure 3C:
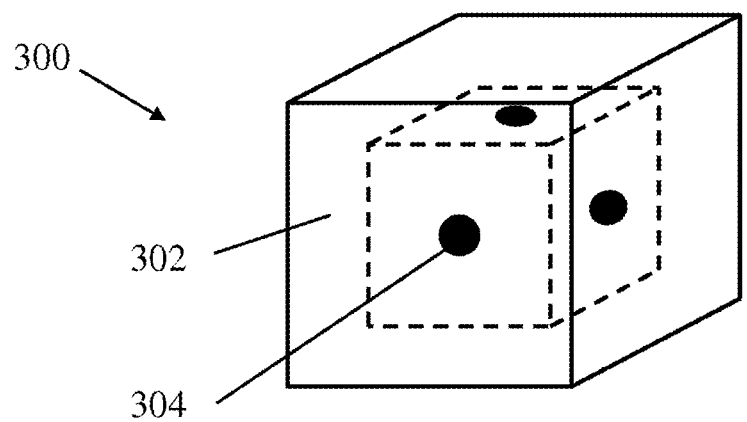
FIG. 3C is a schematic representation of the self-assembling structure of FIG. 3A after swelling.

FIG. 3C depicts a schematic representation of one embodiment of a cubic self-assembling structure 300 that swells in an in vivo environment. The dashed lines indicate the original size of the cube, which corresponds to the physical location of the attachment points 304. As the cube swells, the surfaces 302 of the cube extend outwards such that the spacing between attachment points on adjacent structures increases. Such swelling of the structures may cause physical separation of adjacent attachment points weakening, and ultimately breaking, the bond between the attachment points. For example, in embodiments employing magnets as the attachment points, as the magnets are displaced further from one another due to swelling of the individual structures, the magnetic interactions may become too weak to maintain the structural integrity of an aggregate structure.

In some embodiments, a plurality of self-assembling structures may include two or more separate populations of structures having attachment points which are configured to only interact within a single population. For example, in one embodiment, two populations of self-assembling structures include magnetic attachment points with an arrangement of magnetic orientations that will not form a completed aggregate structure when mixed with one another. In other words, the attachment points of each population are configures such that they are only capable of forming a completed aggregate structure with other structures of that population. Such embodiments may be advantageous as they may allow for the formation of multiple independent aggregate structures which may have different sizes and/or shapes, may comprise different active substances, and/or may be retained internally in a subject for different periods of time. In one such embodiment, the first population may have an arrangement of attachment points with a first set of magnetic orientations, and the second population may have an arrangement of attachment points with a reverse set of magnetic orientations. In another embodiment, the attachment points may be located at different positions on a structure such as one population having attachment points along the center of each side and the other population having attachment points at the corners or non-centered positions of the sides. In instances where non-magnetic based attachment is used, a similar strategy may be used, or the populations may include different compounds that do not bond to the compounds used in the other population.

Figure 4:
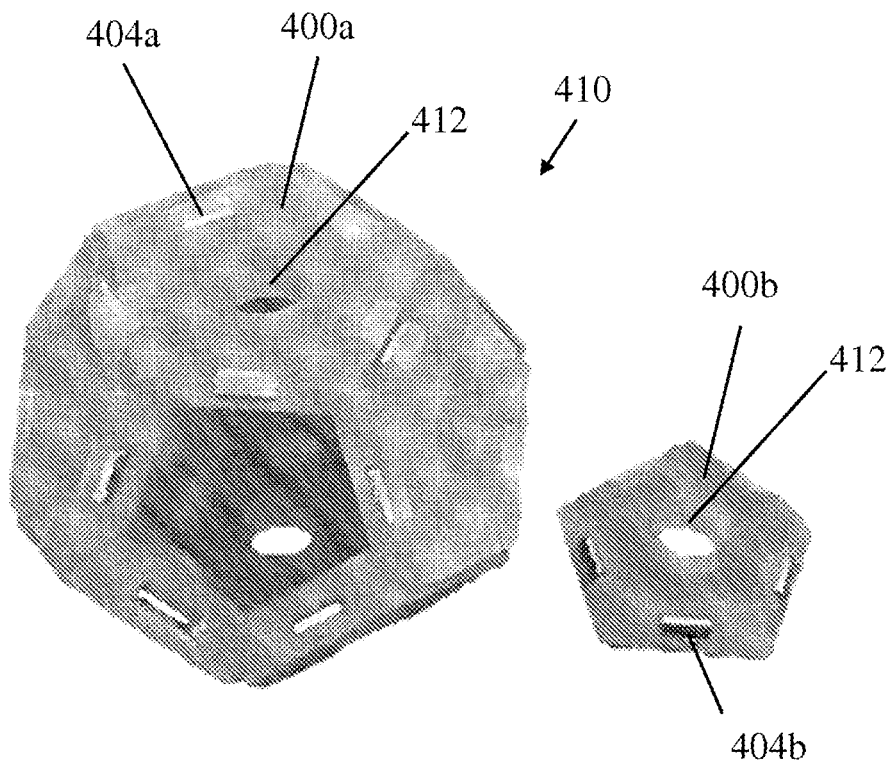
FIG. 4 is a photograph of one embodiment of a dodecahedral aggregate structure.

FIG. 4 depicts one embodiment of a two populations that do not assemble with one another. As illustrated in the figures, a first population of structures 400a have assembled to form a partially formed dodecahedral structure 410. The structures 400a include magnetic attachment points 404a with a first arrangement of magnetic orientations. The structure 400b includes magnetic attachment points 404b with a second set of magnetic orientations that is opposite from the first such that the structure 400b may not assemble onto the aggregate structure 410. As noted above, other arrangements and types of self-assembly control for different populations may be used.

Typical residence devices known in the art such as intragastric balloons generally result in at least partial gastric outlet obstruction in subjects. Therefore, in some embodiments, it may be desirable to permit the passage of food matter through an aggregate structure. By permitting the passage of food matter through the aggregate structure, such a device may help to avoid partial or complete gastric outlet obstruction when the device is located in an internal orifice. In one such embodiment, one or more self-assembling structures used to form an aggregate structure may be sized and shaped to have sufficient void space, through holes/fenestrations, or other appropriate structures that permit the passage of food material, including indigestible substances, through the aggregate structure. Referring again to FIG. 4, an exemplary embodiment of one such device includes a plurality of self-assembling structures where each structure includes a through hole 412 (otherwise known as a fenestration) such that food and other substances may pass through the aggregate structure. In some instances, features, such as the depicted through holes, may also improve the ability of a residence device to release an active agent by increasing the accessible surface area of the structure. In the depicted embodiment, a single circular through hole is illustrated. However, it should be understood that other shapes, multiple through holes, and different sized through holes may be used as the disclosure is not so limited.

In some embodiments, each structure of a plurality of self-assembling structures may comprise an elastic polymer. In certain embodiments, the use of an elastic polymer may impart particular mechanical properties to a self-assembled residence device. For example, in some cases, the device may be capable of undergoing relatively high compressive forces (e.g., compressive forces present within the stomach and/or intestine of a subject) such that the device does not break and/or is retained at a location internally of the subject (e.g., at or above an orifice such as the pylorus). In certain embodiments, the self-assembled structures may be capable of being folded (e.g., does not break on folding). For example, a self-assembling structure comprising an elastic polymer may be capable of undergoing relatively high levels of bending stresses without breaking and/or being significantly permanently deformed. In some embodiments, the elastic polymer and/or the self-assembling structure may be capable of substantial recoil. That is to say, after mechanically deforming the elastic polymer, and/or the self-assembling structure comprising the elastic polymer, may return substantially to its original configuration prior to the mechanical deformation being applied (e.g. the structure may undergo substantially minimal creep and/or plastic deformation).

Several screening tests may be used to determine suitable materials. For example, a structure comprising an elastic polymer may be capable of undergoing at least about 45 degrees, at least about 60 degrees, at least about 90 degrees, at least about 120 degrees, at least about 150 degrees, or about 180 degrees of mechanical bending deformation without breaking. In certain embodiments, the structure may be capable of undergoing less than or equal to about 180 degrees, less than or equal to about 150 degrees, less than or equal to about 120 degrees, less than or equal to about 90 degrees, or less than or equal to about 60 degrees of mechanical bending deformation without breaking. Combinations of the above-referenced ranges are also possible (e.g., between about 45 degrees and about 180 degrees, between about 60 degrees and about 180 degrees, between about 60 degrees and about 120 degrees, between about 90 degrees and about 180 degrees). Other ranges are also contemplated.

In some cases, a self-assembling structure comprising an elastic polymer may be capable of remaining in a deformed configuration (e.g., at least about 45 degrees of mechanical bending deformation) for a relatively prolonged period of time. For example, in some embodiments, a self-assembling structure has a shelf-life in a deformed configuration (e.g., at least about 45 degrees of mechanical bending deformation) of at least about 24 hours, 1 week, 1 month, 1 year, 2 years, or any other appropriate time and be capable of returning (i.e. recoiling) substantially to its pre-deformation configuration. In certain embodiments, the structure has a shelf life in a deformed configuration of less than or equal to about 3 years, 2 years, 1 year, 1 month, 1 week, or any other appropriate time and be capable of returning (i.e. recoiling) substantially to its pre-deformation configuration. Combinations of the above-referenced ranges are also possible (e.g., between about 24 hours and about 3 years, between about 1 week and 1 year, between about 1 year and 3 years). Other ranges are also possible.

In some embodiments, a self-assembling structure comprising an elastic polymer is relatively flexible. In certain embodiments, the elastic polymer may be selected such that it the structure is capable of undergoing large angle deformation for relatively long periods of time without undergoing significant non-elastic deformation. In some such embodiments, the self-assembling structure comprising an elastic polymer may have a strength of recoil sufficient to substantially return the structure to its pre-deformed shape within less than about 30 minutes, 10 minutes, 5 minutes, 1 minute, or any other appropriate time after release of the mechanical deformation. Those skilled in the art would understand that returning to its pre-deformed shape shall be understood to not require absolute conformance to a mathematical definition of shape, but, rather, shall be understood to indicate conformance to the mathematical definition of shape to the extent possible for the subject matter so characterized as would be understood by one skilled in the art most closely related to such subject matter.

In some embodiments, an elastic polymer has a particular elastic modulus. In some embodiments, the elastic modulus of the elastic polymer ranges between about 0.1 MPa and about 30 MPa. In some embodiments, the elastic modulus is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 20 MPa, or at least about 25 MPa. In certain embodiments, the elastic modulus of the elastic polymer is less than or equal to about 30 MPa, less than or equal to about 25 MPa, less than or equal to about 20 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Combinations of the above referenced ranges are also possible (e.g., between about 0.1 MPa and about 30 MPa, between about 0.3 MPa and about 10 MPa). Other ranges are also possible. Those skilled in the art would be capable of selecting suitable methods for determining the elastic modulus of a polymeric component including, for example, tensile mechanical characterization under ASTM D638 and/or compressive mechanical characterization under ASTM D575.

In some embodiments, a self-assembling structure comprising an elastic polymer undergoes a relatively low amount of creep during mechanical deformation. For example, in certain embodiments, the structure has a minimum creep rate of less than or equal to about 0.3 mm/mm/hr, 0.2 mm/mm/hr, 0.1 mm/mm/hr, 0.08 mm/mm/hr, 0.05 mm/mm/hr, 0.03 mm/mm/hr, or 0.02 mm/mm/hr. In certain embodiments, the structure has a minimum creep rate of at least about 0.01 mm/mm/hr, 0.02 mm/mm/hr, 0.03 mm/mm/hr, 0.05 mm/mm/hr, 0.08 mm/mm/hr, 0.1 mm/mm/hr, or 0.2 mm/mm/hr. Combinations of the above referenced ranges are also possible (e.g., between about 0.01 mm/mm/hr and about 0.3 mm/mm/hr, between about 0.02 mm/mm/hr and about 0.1 mm/mm/hr, between about 0.02 mm/mm/hr and about 0.05 mm/mm/hr, between about 0.05 mm/mm/hr and about 0.3 mm/mm/hr). Other ranges are also possible. Minimum creep rate can be determined, in some embodiments, according to ASTM D-638. Briefly, a sheet of the elastic polymeric material is prepared and cut using a standard dumbbell die. The specimens can be loaded into grips of an Instron testing machine and the gauge length measured using a digital micrometer. A constant stress corresponding to 30% of the ultimate tensile strength of each material may be applied to the specimens for 60 min at constant temperature (e.g., room temperature) and the creep (in mm/mm) versus time (in hours) can be plotted. The minimum creep rate is the slope of the creep vs. time curve prior to secondary creep.

Those skilled in the art would be capable of determining suitable methods for tuning the mechanical properties (e.g., elastic modulus, creep behavior) of the elastic polymeric component by, for example, varying the molar ratios of monomeric and/or polymeric units (e.g., increasing the amount of high molecular weight polycaprolactone or other polymers used in the elastic polymeric component), varying polymer cross-linking density, varying the concentration of cross-linking agents used in the formation of the polymer, varying the crystallinity of the polymer (e.g., by varying the ratio of crystalline and amorphous regions in the polymer) and/or the use of additional or alternative materials (e.g., incorporating materials such as bis(isocyanatomethyl)-cyclohexane).

In some embodiments, a self-assembling structure comprising an elastic polymer is generally biocompatible. The term "biocompatible," as used herein, refers to a polymer that does not invoke an adverse reaction (e.g., immune response) from an organism (e.g., a mammal), a tissue culture or a collection of cells, or if an adverse reaction does occur it does not exceed an acceptable level. In some embodiments, a self-assembling structure comprises polymers, their networks, and/or multi-block combinations of, for example, polyesters, including but not limited to, polycaprolactone, poly(propylene fumarate), poly(glycerol sebacate), poly(lactide), poly(glycol acid), poly(lactic-glycolic acid), polybutyrate, and polyhydroxyalkanoate; polyethers, including but not limited to, poly(ethylene oxide) and poly (propylene oxide); polysiloxanes, including but not limited to, poly(dimethylsiloxane); polyamides, including but not limited to, poly(caprolactam); polyolefins, including but not limited to, polyethylene; polycarbonates, including but not limited to poly(propylene oxide); polyketals; polyvinyl alcohols; polyoxetanes; polyacrylates/methacrylates, including but not limited to, poly(methyl methacrylate) and poly (ethyl-vinyl acetate); polyanhydrides; and polyurethanes. In some embodiments, the polymer is cross-linked. In some embodiments, the self-assembling structure comprises a polymer composite comprising two or more chemically similar polymers or two or more chemically distinct polymers.

In some embodiments, a self-assembling structure comprises an enteric polymer. The term enteric is generally used to describe materials that are stable at relatively highly acidic pH conditions (e.g., pH of less than about 5.5) and susceptible to dissolution at relatively alkaline pH conditions (e.g., pH of between about 6 and about 9). In some embodiments, the enteric polymer includes, but is not limited to, cellulose acetate phthalate (CAP), hypromellose (INN) hydroxypropyl methylcellulose (HPMC), and/or poly (methacrylic acid-co-ethyl acrylate) (e.g., EUDRAGIT® a available from Evonik Industries AG (Essen, Germany)).

In some embodiments, the dissolution of an enteric polymer can be triggered by, for example, ingestion of an alkali solution. In some embodiments, the enteric polymer dissolves at pH's between about 4-8. According to some embodiments, the enteric polymer is selected such that the enteric polymer is stable in an acidic gastric environment (i.e., having a pH1 to pH4) but dissolves in a more alkali region of the gastrointestinal tract distal to the pylorus (i.e., having a pH greater than 5.5) and can serve as a self-assembling structure.

For example, in certain embodiments, the enteric polymer does not substantially degrade at a pH ranging between about 1 and about 5. In some embodiments, the enteric polymer does not substantially degrade at a pH of at least about 1, at least about 2, at least about 3, at least about 4, or at least about 4.5. In certain embodiments, the enteric polymer does not substantially degrade at a pH of less than or equal to about 5, less than or equal to about 4.5, less than or equal to about 4, less than or equal to about 3, or less than or equal to about 2. Combinations of the above reference ranges are also possible (e.g., between about 1 and about 4.5, between about 1 and about 5, between about 1 and 4). Other ranges are also possible.

In certain embodiments, the enteric polymer degrades substantially at a pH ranging between about 4 and about 8. In some embodiments, the enteric polymer degrades substantially at a pH of at least about 4, at least about 5, at least about 6, at least about 6.5, at least about 7, or at least about 7.5. In certain embodiments, the enteric polymer degrades substantially at a pH of less than or equal to about 8, less than or equal to about 7.5, less than or equal to about 7, less than or equal to about 6.5, less than or equal to about 6, or less than or equal to about 5. Accommodations of the above reference ranges are also possible (e.g., between about 4 and about 8, between about 5 and about 8, between about 6.5 and about 7.5). Other ranges are also possible.

Those skilled in the art would be capable of selecting suitable methods for determining degradation of the enteric polymers based upon the teachings of the specification including, determining the solubility of the enteric polymer in an aqueous solution having a pH of less than about 3 and/or dissolving the enteric polymer in aqueous solution having a pH of greater than or equal to about 6, measured at body temperature (e.g., between about 35° C. and about 38° C.) over time period of between about 2 and about 40 days.

According to some embodiments, a device is configured to maintain safety with low to no potential for intestinal obstruction and/or perforation. Controlled degradation is important, in some cases, for mitigating the risk of gastrointestinal obstruction. In some embodiments, a self-assembling structure is configured to dissolve distal to the pylorus. As discussed above, in some embodiments, a residence device comprising a self-assembled aggregate structure is configured such that upon degradation/dissolution of one or more self-assembling structures, the device breaks into smaller structures capable of passing through a gastrointestinal tract (e.g., traversing the ileocecal valve) without obstruction. In an illustrative embodiment, the self-assembling structures do not substantially dissolve and/or degrade when located in the stomach of a subject (e.g., having a pH ranging between about 1 and about 5) and substantially degrades when located (e.g., after passing through the pylorus) in the intestines (e.g., having a pH ranging between about 6.7 and about 7.4).

In certain embodiments, the enteric elastomer is capable of exhibiting reversible elongation when stretched from 50% to 1500% of its initial length. For example, in some embodiments, the enteric elastomer is capable of exhibiting reversible elongation when stretched from at least about 50%, at least about 100%, at least about 200%, at least about 400%, at least about 500%, at least about 1000%, at least about 1200%, or at least about 1400% of its initial length. That is to say, in some embodiments, the enteric elastomer has difference in average length after deformation versus before deformation (e.g., stretching) of less than about 10%, less than about 5%, less than about 2%, or less than about 1%. In certain embodiment, the enteric elastomer is capable of exhibiting reversible elongation when stretched from less than or equal to about 1500%, less than or equal to about 1400%, less than or equal to about 1200%, less than or equal to about 1000%, less than or equal to about 500%, less than or equal to about 400%, less than or equal to about 200%, or less than or equal to about 100% of its initial length. Any and all closed ranges that have endpoints within any of the above referenced ranges are also possible (e.g., between about 50% and about 1500%, between about hundred percent and about 1500%, between about 200% and about 1000%, between about 500% and about 1400%). Other ranges are also possible.

In certain embodiments, the enteric elastomer has an elastic modulus ranging between about 0.1 MPa and about 100 MPa. In some embodiments, the elastic modulus of the enteric elastomer is at least about 0.1 MPa, at least about 0.2 MPa, at least about 0.3 MPa, at least about 0.5 MPa, at least about 1 MPa, at least about 2 MPa, at least about 5 MPa, at least about 10 MPa, at least about 25 MPa, or at least about 50 MPa. In certain embodiments, the elastic modulus of the enteric elastomer is less than or equal to about 100 MPa, less than or equal to about 50 MPa, less than or equal to about 25 MPa, less than or equal to about 10 MPa, less than or equal to about 5 MPa, less than or equal to about 2 MPa, less than or equal to about 1 MPa, less than or equal to about 0.5 MPa, less than or equal to about 0.3 MPa, or less than or equal to about 0.2 MPa. Combinations of the above referenced ranges are also possible (e.g., between about 0.1 MPa and about 100 MPa, between about 0.3 MPa and about 10 MPa). Other ranges are also possible. Those skilled in the art would be capable of selecting suitable methods for determining the elastic modulus of an enteric elastomer including, for example, tensile mechanical characterization under ASTM D638 and/or compressive mechanical characterization under ASTM D575.

In certain embodiments, the enteric elastomer comprises a polymeric mixture of varying ratios of poly(acryloyl-6-aminocaproic acid) and poly(methacrylic acid-co-ethyl acrylate).

In some embodiments, the enteric elastomer comprises a polymer of a acryloylaminoalkylene acid monomer, or salts thereof. In some embodiments, the polymer composite comprises a polymer of an acryloylaminoalkylene acid monomer, a (meth)acryloylaminoalkylene acid monomer, or salts thereof. In certain embodiments, the acryloylaminoalkylene acid monomer is selected from the group consisting of acryloyl-5-aminopentanoic acid, acryloyl-6-aminocaproic acid, acryloyl-7-aminoheptanoic acid, acryloyl-8-aminooctanoic acid, acryloyl-9-aminononanoic acid, acryloyl-10-aminodecanoic acid, acryloyl-11-aminoundecanoic acid, acryloyl-12-aminododecanoic acid, methacryloyl-5-aminopentanoic acid, methacryloyl-6-aminocaproic acid, methacryloyl-7-aminoheptanoic acid, methacryloyl-8-aminooctanoic acid, methacryloyl-9-aminononanoic acid, methacryloyl-10-aminodecanoic acid, methacryloyl-11-aminoundecanoic acid, methacryloyl-12-aminododecanoic acid, salts thereof, and combinations thereof.

In certain embodiments, the enteric elastomer comprises a homopolymer of acryloyl-6-aminocaproic acid or salts thereof. In some embodiments, the enteric elastomer comprises a copolymer of acryloyl-6-aminocaproic acid or salts thereof. In certain embodiments, enteric elastomer comprises poly(methacrylic acid-co-ethyl acrylate) or salts thereof. In some cases, the poly(methacrylic acid-co-ethyl acrylate) has a molar ratio of methacrylic acid monomer units to ethylacrylate monomer units of about 1:1.

In some embodiments, the enteric elastomer is a blend. For example, in certain embodiments, the enteric elastomer comprises a first enteric polymer (e.g., poly(acryloyl-6-aminocaproic acid)) and a second enteric polymer (e.g., poly(methacrylic acid-co-ethyl acrylate)). In some such embodiments, the weight ratio of the first polymer to the second polymer ranges from about 1:6 to about 6:1. In certain embodiments, the weight ratio of the first polymer to the second polymer is at least about 1:6, at least about 1:5, at least about 1:4, at least about 1:3, at least about 1:2, at least about 1:1, at least about 2:1, at least about 3:1, at least about 4:1, or at least about 5:1. In some embodiments, the weight ratio of the first polymer to the second polymer is less than or equal to about 6:1, less than or equal to about 5:1, less than or equal to about 4:1, 3:1, less than or equal to about 2:1, less than or equal to about 1:1, less than or equal to about 1:2, less than or equal to about 1:3, less than or equal to about 1:4, or less than or equal to about 1:5. Combinations of the above referenced ranges are also possible (e.g., between about 1:6 and about 6:1, between about 1:4 and about 4:1, between about 1:3 and about 3:1, between about 1:2 and about 2:1, between about 1:3 and about 1:1, between about 1:1 and about 3:1). Other ranges are also possible.

In some embodiments, the enteric elastomer is a polymer gel with water content no greater than 40%. For example, in some embodiments, the polymer composite has a water content of less than or equal to about 40 wt %, less than or equal to about 30 wt %, less than or equal to about 20 wt %, or less than or equal to about 10 wt %. In some embodiments, the polymer composite has a water content greater than about 5 wt %, greater than about 10 wt %, greater than about 20 wt %, or greater than about 30 wt %. Combinations of the above-referenced ranges are also possible (e.g., between about 5 wt % and about 40 wt %).

The enteric elastomer can be used as a material platform. In some embodiments, this material platform features tunable elastomeric properties, is stable in an acidic environment, and/or dissolvable in a more alkali environment. Thus, the enteric elastomer material platform is compatible with the acidic gastric environment and has the capacity for targeted dissolution in the small intestinal/colonic environment. According to some embodiments, the enteric elastomer material platform is useful for many applications, including, but not limited to, gastrointestinal structure manufacturing, and gastrointestinal-specific drug delivery with targeted release beyond the pylorus.

For example, one or more enteric elastomer polymers attached to and/or incorporated into a device in a gastric cavity would mitigate the risk of accidental passage of the aggregate structure, which could induce obstruction and/or penetration, because the rapid dissolution of the one or more self-assembling structures upon passage through the pylorus would reduce the aggregate structure to smaller structures.

A structure bonded with an enteric elastomer is subject to dissolution in the presence of an alkali environment. Thus, in the case of a gastric device resident in vivo and comprising an enteric elastomer, passage of the device can be induced if the subject ingests an alkali solution (e.g., sodium bicarbonate) to induce the dissolution of the enteric elastomer to enable breakdown of the device in accordance with some embodiments.

In some embodiments, the enteric elastomer has great flexibility. Flexibility can enable packing and/or folding of a structure to, for example, fit into a confined/predefined vessel such as capsule for oral administration or a catheter for endoscopic deployment, as described herein. In some embodiments, the enteric elastomer has flexibility to 180 degrees to enable tight and/or maximal packing and/or folding.

In some embodiments, one or more components may comprise a food grade cross-linked (FGC) polymer. For example, in certain embodiments, one or more self-assembling structures comprises a food grade catalyst catalyzed polymer. In some embodiments, the food grade cross-linked polymer comprises food grade ingredients cross-linked and/or polymerized using a food grade catalyst. Food grade cross-linked polymers generally may have advantageous combinations of properties including mechanical strength, biocompatibility and/or moldability. In some cases, the FGC polymer advantageously can provide controlled release of the therapeutic agent, while comprising little to no auxiliary materials (e.g., solvents, catalysts, excipients) which, in some cases, may be toxic agents. In some embodiments, the FGC polymer is formed by the reaction of one or more monomers in the presence of a food grade catalyst. The use of food grade catalysts to form FGC polymers offers several advantages including, for example, the formation of components which contain primarily (or only) FDA approved ingredients and biocompatibility. In certain embodiments, the FGC polymer comprises ester bonds such that, for example, the FGC polymer is degradable under physiological conditions. Advantageously, the FGC polymer may comprise a polymeric material (e.g., a thermoset polymeric material) having the strength and integrity of epoxy resins, the biomedical applicability of hydrogels, and/or the moldability of vitrimers.

In some embodiments, the FGC polymer is cross-linked. In certain embodiments, the FGC polymer is substantially amorphous. In one embodiment, the FGC polymer is a derived from oligomeric or polymeric strands or chains which have undergone crosslinking via reactions that do not preclude inclusion of sensitive therapeutics (e.g., active substances may be loaded and released directly into the FGC polymer). The FGC polymer may be softer than conventional hardened resins and may be characterized by a lower Young's modulus and crosslinking density than conventional hardened resins. In contrast to a shape memory polymer which generally returns to its original form after it has been stretched or otherwise stressed, the FGC polymer remains fixed in its new shape after it has been molded into a new position.

In some embodiments, the FGC polymer is formed by the reaction of two or more polyfunctional monomers (e.g., a first polyfunctional monomer and a second polyfunctional monomer). In certain embodiments, the FGC polymer is formed by the reaction of two or more, three or more, four or more, or five or more polyfunctional monomers. In some embodiments, each polyfunctional monomer comprises a reactive functional group. In certain embodiments, two or more reactive functional groups may form a covalent bond with one another. For example, in some cases, the reaction of a first reactive functional group and a second reactive functional group forms a covalent bond between the first reactive functional group and the second reactive functional group. In other embodiments, the reaction between two or more reactive functional groups is a Michael-addition. In other embodiments, the reaction between two or more reactive functional groups is a cycloaddition reaction, especially a Diels-Alder reaction.

In some embodiments, one or more polyfunctional monomers is bifunctional. In certain embodiments, one or more polyfunctional monomers is trifunctional. In some cases, one or more polyfunctional monomers may be tetrafunctional, pentafunctional, hexafunctional, or have higher orders of functionality. In a particular embodiments, the FGC polymer is formed by the reaction of one or more bifunctional monomers and one or more trifunctional monomers.

In one embodiment, the FGC polymer may be represented by Formula (I).

Formula (I)

wherein A is derived from at least one polyfunctional monomer containing at least two reactive functional groups, and B is derived from at least one polyfunctional monomer containing at least two reactive functional groups, and wherein the compound of Formula (I) comprises crosslinked bonds. For example, in a particular embodiment, the FGC polymer comprising the structure as in Formula (I) is formed by the reaction of a first polyfunctional monomer comprising two reactive functional groups and a second polyfunctional comprising three reactive functional groups. In another embodiment, the FGC polymer comprising the structure as in Formula (I) is formed by the reaction of a first polyfunctional monomer comprising two reactive functional groups, a second polyfunctional monomer different than the first polyfunctional monomer comprising two reactive functional groups, and a third polyfunctional monomer comprising three reactive functional groups. In some such embodiments, the reactive functional groups of the first polyfunctional monomer may be the same or different as the reactive functional groups of the second polyfunctional monomer and/or the third polyfunctional monomer. For example, the reactive groups of the first polyfunctional monomer may react with (and form a covalent bond with) the reactive groups of the second polyfunctional monomer and/or the third polyfunctional monomer.

In some embodiments, one or more polyfunctional monomers contain an oligomeric moiety. In certain embodiments, the FGC polymer of Formula (I) is further characterized by the presence of at least two reactive groups capable of forming a crosslink bond.

In certain embodiments, the compound of Formula (I) is prepared by combining two or more polyfunctional monomers, and then incubating the mixture at a temperature sufficient to initiate polymerization to reach the gel point. In some embodiments, the two or more polyfunctional monomers are combined in the presence of a catalyst. In certain embodiments, two or more polyfunctional monomers are combined in the presence of a subunit compound, in the presence of an active substance, or both.

In some embodiments, the polyfunctional monomer has a structure as in Formula (II):

Q1-L-Q2     (II)

wherein Q1 and Q2 are the same or different and a reactive functional group and L has a structure as in Formula (III):

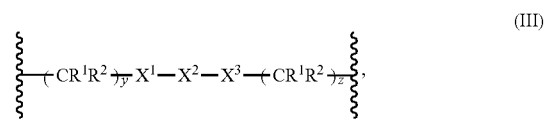

(III)

wherein ⁞ indicates a point of connection to $Q^1$ and $Q^2$.

In some embodiments, the polyfunctional monomer has a structure as in:

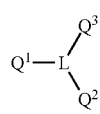

wherein Q1, Q2, and Q3 are the same or different and a reactive functional group and L has a structure as in Formula (III).

In some embodiments, X1, X2, and X3 are the same or different and are absent or selected from the group consisting of (CR1R2)m, a heteroatom, an alkenyl, an alkynyl, a cycloalkyl, an aryl, a heterocyclic group, a heteroaryl group, and an oligomeric group. In certain embodiments, X1, X2, and/or X3 are absent.

In certain embodiments, m is zero or any integer. For example, in some embodiments, m is 0. In certain embodiments, m is 1-3, 2-4, 3-6, 4-8, 5-10, 8-16, 12-24, 20-30, 25-50, 40-60, 50-100, 75-150, 125-200, 150-300, 250-500, 400-600, 500-800, or 750-1500. In some cases, m is 1-3. In certain embodiments, m is 2-4. In some cases, m is 4-8. In some embodiments, m is 8-16. The value of m may be selected to impart certain properties in the FGC polymer (e.g., crosslink density, Young's elastic modulus).

In some embodiments, y is zero or any integer. For example, in some embodiments, y is 0. In certain embodiments, y is 1-3, 2-4, 3-6, 4-8, 5-10, 8-16, 12-24, 20-30, 25-50, 40-60, 50-100, 75-150, 125-200, 150-300, 250-500, 400-600, 500-800, or 750-1500. In some cases, y is 1-3. In certain embodiments, y is 2-4. In some cases, y is 4-8. In some embodiments, y is 8-16. The value of y may be selected to impart certain properties in the FGC polymer (e.g., crosslink density, Young's elastic modulus).

In certain embodiments, z is zero or any integer. For example, in some embodiments, z is 0. In certain embodiments, z is 1-3, 2-4, 3-6, 4-8, 5-10, 8-16, 12-24, 20-30, 25-50, 40-60, 50-100, 75-150, 125-200, 150-300, 250-500, 400-600, 500-800, or 750-1500. In some cases, z is 1-3. In certain embodiments, z is 2-4. In some cases, z is 4-8. In some embodiments, z is 8-16. The value of z may be selected to impart certain properties in the FGC polymer (e.g., crosslink density, Young's elastic modulus).

In a particular embodiment, m+y+z is zero. In certain embodiments, m+y+z is 1. In some cases, m+y+z is an integer and is 2 or greater.

In some embodiments, each R1 and R2 are the same or different and are selected from the group consisting of hydrogen, an aliphatic group, a halogen, a hydroxyl, a carbonyl, a thiocarbonyl, an oxo, an alkoxy, an epoxy, a phosphoryl, a phosphate, a phosphonate, a phosphinate, an amino, an amido, an amidine, an imine, a cyano, a nitro, an azido, a thiol, an alkylthio, a sulfate, a sulfonate, a sulfamoyl, a sulfonamido, a sulfonyl, a cycloalkyl, a heterocyclyl, an aralkyl, and an aromatic or heteroaromatic or a Michael acceptor, wherein any two or more R1 and R2 groups may be bonded together so as to form a ring system. In certain embodiments, each R1 and/or R2 may be Q3 (i.e. a reactive functional group).

In an exemplary embodiment, the polyfunctional monomer has the structure as in Formula (IV):

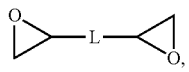
(IV)

wherein L is as described above. In another exemplary embodiments, the polyfunctional monomer has the structure as in:

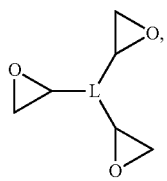

wherein L is as described above. In yet another exemplary embodiment, the polyfunctional monomer has a structure as in Formula (V) or Formula (VI):

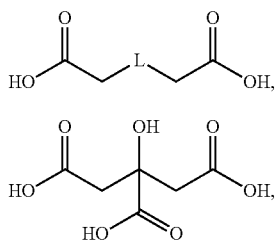
(V)
(VI)

wherein L is described above. In some embodiments, the FGC polymer is formed by the reaction of a first polyfunctional monomer having a structure as in Formula (IV) with a second polyfunctional monomer having a structure as in Formula (V) or Formula (VI).

Polyfunctional monomers described herein may comprise at least two, at least three, at least four, or at least five reactive functional groups. For example, in some embodiments, Q1, Q2, and Q3 may be the same or different and an electrophilic functional groups or a nucleophilic functional group.

In some embodiments, one or more reactive groups (e.g., Q1, Q2, and/or Q3) is an electrophilic functional groups. For example, a monomer may comprise at least two, at least three, at least four, or at least five electrophilic functional groups. Non-limiting examples of suitable electrophilic functional groups include alkenes, alkynes, esters (e.g., N-hydroxysuccinimide ester), acrylates, methacrylates, acyl halides, acyl nitriles, alkyl halides, aldehydes, ketones, alkyl sulfonates, anhydrides, epoxides, haloacetamides, aziridines, and diazoalkanes.

In certain embodiments, one or more reactive functional groups (e.g., Q1, Q2, and/or Q3) is a nucleophilic functional groups. For example, a monomer may comprise at least two, at least three, at least four, or at least five nucleophile reactive functional groups. Non-limiting examples of suitable nucleophilic functional groups include alcohols, amines, anilines, phenols, hydrazines, hydoxylamines, carboxylic acids, alkoxide salts, alkenes, thiols, and glycols.

The polyfunctional monomers described herein may comprise at least one electrophilic functional group and at least one nucleophilic functional group. For example, in an exemplary embodiment, the first polyfunctional monomer comprises both an electrophilic functional group and a nucleophilic functional group. In certain embodiments, the first polyfunctional monomer comprises two or more electrophile functional groups and the second polyfunctional monomer comprises two or more nucleophile functional groups.

In some cases, the reaction of an electrophilic functional group and a nucleophilic functional group form a bioresponsive bond such as an ester bond, an ether bond, an amide bond, an amine bond, or a thioether bond. For example, in certain embodiments, the FGC polymer comprises an ester bond formed by the reaction of an electrophilic functional group and a nucleophilic functional group. In some embodiments, the FGC polymer comprises an ether bond formed by the reaction of an electrophilic functional group and a nucleophilic functional group. Other bonds are also possible.

In some embodiments the FGC polymer is formed by the reaction of two or more polyfunctional monomers and an additional monomeric unit. In some embodiments, the additional monomeric unit comprises a compound containing one or more carboxylic acid derivatives. In some embodiments, the additional monomeric unit is a single compound containing at least one ester, amide or thioester group, or a mixture of compounds containing at least one ester, amide or thioester. In certain embodiments, the additional monomeric unit is a compound containing a lactone, lactam or thiolactone group. In certain embodiments, the additional monomeric unit is a naturally occurring lactone or lactam. In another embodiment, the additional monomeric unit lactone-containing or lactam-containing compound selected from the FDA's "Generally Recognized as Safe" Substances database and/or listed in 21 C.F.R. § 182. In certain embodiments, the additional monomeric unit is selected γ-decalactone, δ-decalactone, ω-pentadecalactone, caprolactam, and mixtures thereof.

In certain embodiments, the additional monomeric unit does not contain a primary or secondary amine moiety.

In some embodiments, the molar ratio of the first polyfunctional monomer (e.g., comprising electrophilic reactive groups) to a mixture of additional polyfunctional monomers (e.g., comprising nucleophilic reactive groups) and/or additional monomeric units ranges between about 10:1 and about 1:10. In an exemplary embodiment, the molar ratio of the first polyfunctional monomer to a mixture of additional polyfunctional monomers and/or monomeric units is about 1:1. In certain embodiments, the molar ratio of first polyfunctional monomer to a mixture of additional polyfunctional monomers and/or monomeric units is at less than about 10:1, less than about 8:1, less than about 6:1, less than about 4:1, less than about 2:1, less than about 1.5:1, less than about 1:1, less than about 1.5:1, less than about 1:2, less than about 1:4, less than about 1:6, or less than about 1:8. In some embodiments, the molar ratio of first polyfunctional monomer to a mixture of additional polyfunctional monomers and/or monomeric units is greater than or equal to about 1:10, greater than or equal to about 1:8, greater than or equal to about 1:6, greater than or equal to about 1:4, greater than or equal to about 1:2, greater than or equal to about 1:1.5, greater than or equal to about 1:1, greater than or equal to about 1.5:1, greater than or equal to about 2:1, greater than or equal to about 4:1, greater than or equal to about 6:1, or greater than or equal to about 8:1. Combinations of the above-referenced ranges are also possible (e.g., between about 10:1 and about 1:10, between about 1:4 and about 4:1, between about 1:2 and about 2:1).

In some such embodiments, the second polyfunctional monomer is present in the mixture of additional polyfunctional monomers and/or monomeric units in an amount of at least about 10 mol %, at least about 20 mol %, at least about 25 mol %, at least about 50 mol %, at least about 75 mol %, at least about 90 mol %, or at least about 99 mol %. In certain embodiments, the second polyfunctional monomer is present in the mixture of additional polyfunctional monomers and/or monomeric units in an amount of less than or equal to about 99.9 mol %, less than or equal to about 99 mol %, less than or equal to about 90 mol %, less than or equal to about 75 mol %, less than or equal to about 50 mol %, less than or equal to about 25 mol %, or less than or equal to about 20 mol %. Combinations of the above-referenced ranges are also possible (e.g., between about 25 mol % and about 99.9 mol %). Other ranges are also possible.

As described above, in some embodiments, two or more polyfunctional monomers are combined (i.e. reacted) in the presence of a catalyst.

In some embodiments, the catalyst is a nucleophile. In certain embodiments, the catalyst is a base (e.g., a mild base, a weak base). In certain embodiments, the catalyst is a metal salt. In some embodiments, the catalyst is a sulfate salt of zinc such as ZnSO4 and hydrates thereof.

In some embodiments, the catalyst is selected from catalysts listed in FDA's "Generally Recognized as Safe" Substances database and/or listed in 21 C.F.R. § 182. In certain embodiments, the catalyst is food grade and/or food derived catalyst.

In certain embodiments, the catalyst is an organic amine. In some embodiments, the catalyst is a tertiary amine. In some cases, the tertiary amine catalyst does not contain any amino N—H or NH2 functional groups.

In some embodiments, the catalyst is an alkaloid compound. In certain embodiments, the catalyst is a purine base. Non-limiting examples of purine bases include purine, adenine, guanine, hypoxanthine, xanthine, theobromine, caffeine, uric acid and isoguanine. In an exemplary embodiment, the catalyst is caffeine.

The use of a food grade catalyst such as caffeine generally offers numerous advantages over traditional catalysts including FDA approval, low cytotoxicity, and/or a reduced need (or substantially no need) to remove the catalyst after polymerization.

In some embodiments, the catalyst (e.g., food grade catalyst) is present in the FGC polymer after the formation of the FGC polymer in an amount ranging between 0.01 mol % and about 25 mol %. For example, in some embodiments, the FGC polymer comprises substantially no catalyst after the formation of the FGC polymer. In certain embodiments, the catalyst is present in the FGC polymer after the formation of the FGC polymer in an amount of at least about 0.01 mol %, at least about 0.05 mol %, at least about 0.1 mol %, at least about 0.5 mol %, at least about 1 mol %, at least about 2 mol %, at least about 5 mol %, at least about 10 mol %, or at least about 20 mol %. In certain embodiments, the catalyst is present in the FGC polymer after the formation of the FGC polymer in an amount of less than or equal to about 25 mol %, less than or equal to about 20 mol %, less than or equal to about 10 mol %, less than or equal to about 5 mol %, less than or equal to about 2 mol %, less than or equal to about 1 mol %, less than or equal to about 0.5 mol %, less than or equal to about 0.1 mol %, or less than or equal to about 0.05 mol %. Combinations of the above-referenced ranges are also possible (e.g., between 1 mol % and 25 mol %, between 0.01 mol % and 5 mol %). Other ranges are also possible.

As described above, in some embodiments, the FGC polymer may be formed using three or more polyfunctional monomers. In an exemplary reaction, polypropylene oxide is reacted with citric acid, mercaptosuccinic acid, and PPO-dimethacrylate in the presence of caffeine via Michael addition to form a branched FGC polymer.

In some embodiments, a residence device, and its sub structures (e.g., a plurality of self-assembling structures or an aggregate structure), is pre-loaded with an active substance such as a therapeutic, diagnostic, and/or enhancement agent. In some embodiments, a device is configured to maintain stability of the therapeutic, diagnostic, and/or enhancement agents in a hostile physiological environment (e.g., the gastric environment) for an extended duration. In further embodiments, the device is configured to control release of the therapeutic, diagnostic, and/or enhancement agents with low to no potential for burst release. In some embodiments, the device is pre-loaded with a combination of active substances. For example, in certain embodiments, the device comprises one or more, two or more, three or more, four or more, or any other appropriate number of active substances. In some embodiments, different structures of a plurality of self-assembling structures may comprise different active substances.

Therapeutic, diagnostic, and/or enhancement agents can be loaded into polymeric materials and other drug delivery materials via standard methods including, but not limited to, powder mixing, direct addition, solvent loading, melt loading, physical blending, supercritical carbon dioxide, and conjugation reactions such as ester linkages and amide linkages. Release of therapeutic, diagnostic, and/or enhancement agents can then be accomplished through methods including, but not limited to, dissolution of the components comprising a polymeric matrix material, degradation of the matrix material, swelling of the matrix material, diffusion of an agent, hydrolysis, and/or chemical or enzymatic cleavage of the conjugating bonds. In some embodiments, the active substance is covalently bound to the polymer matrix of the polymeric component (e.g., is released as the polymer matrix degrades).

In certain embodiments, the component is constructed and arranged to release the active substance from the component. Such embodiments may be useful in the context of drug delivery. In other embodiments, the active substance is permanently affixed to the component. Such embodiments may be useful in molecular recognition and purification contexts. In certain embodiments, the active substance is embedded within the component. In some embodiments, the active substance is associated with the component via formation of a bond, such as an ionic bond, a covalent bond, a hydrogen bond, Van der Waals interactions, and the like. The covalent bond may be, for example, carbon-carbon, carbon-oxygen, oxygen-silicon, sulfur-sulfur, phosphorus-nitrogen, carbon-nitrogen, metal-oxygen, or other covalent bonds.

The hydrogen bond may be, for example, between hydroxyl, amine, carboxyl, thiol, and/or similar functional groups.

According to some embodiments, the systems, devices, and methods described herein are compatible with one or more therapeutic, diagnostic, and/or enhancement agents, such as drugs, nutrients, microorganisms, in vivo sensors, and tracers. In some embodiments, the active substance, is a therapeutic, nutraceutical, prophylactic or diagnostic agent. The active substance may be entrapped within the polymeric matrix or may be directly attached to one or more atoms in the polymeric matrix through a chemical bond. In certain embodiments, the active substance is covalently bonded to the polymeric matrix. In some embodiments, the active substance is bonded to the polymeric matrix through a carboxylic acid derivative. In some cases, the carboxylic acid derivative may be an ester bond.

Agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals, Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, non-steroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, antiviral agents like entecavir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In some embodiments, the active substance is a radiopaque material such as tungsten carbide or barium sulfate.

In certain embodiments, the active substance is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, prostaglandins, antimicrobials (including antibiotics, antifungals, antivirals, antiparasitics), antimuscarinics, anxioltyics, bacteriostatic s, immunosuppres sant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery device. These may be vitamins, supplements such as calcium or biotin, or natural ingredients such as plant extracts or phytohormones.

In some embodiments, the therapeutic agent is one or more antimalarial drugs. Exemplary antimalarial drugs include quinine, lumefantrine, chloroquine, amodiaquine, pyrimethamine, proguanil, chlorproguanil-dapsone, sulfonamides such as sulfadoxine and sulfamethoxypyridazine, mefloquine, atovaquone, primaquine, halofantrine, doxycycline, clindamycin, artemisinin and artemisinin derivatives. In some embodiments, the antimalarial drug is artemisinin or a derivative thereof. Exemplary artemisinin derivatives include artemether, dihydroartemisinin, arteether and artesunate. In certain embodiments, the artemisinin derivative is artesunate.

Active substances that contain a carboxylic acid group may be directly incorporated into polymeric matrices that contain ester and hydroxyl groups without further modification. Active substances containing an alcohol may first be derivatized as a succinic or fumaric acid monoester and then incorporated into the polymeric matrix. Active substances that contain a thiol may be incorporated into olefin or acetylene-containing matrices through a sulfur-ene reaction. In other embodiments, the one or more agents are non-covalently associated with the polymeric matrices (e.g., dispersed or encapsulated within).

In other embodiments, the active substance is a protein or other biological macromolecule. Such substances may be covalently bound to the polymeric matrix through ester bonds using available carboxylate containing amino acids, or may be incorporated into polymeric material containing olefinic or acetylenic moieties using a thiol-ene type reaction. In some cases, the active substance comprises an amine functional group capable of reacting with an epoxide functional group to form an amide or ester bond. In other embodiments, the active substance is non-covalently associated with the polymeric matrix. In some such embodiments, the active substance may be dispersed or encapsulated within by hydrophilic and/or hydrophobic forces.

In some cases, the partition coefficient of the active substance in the polymeric material can be tuned. For example, if the active substance is hydrophobic, a hydrophobic polymeric material backbone may, in some cases, slow the release into aqueous solution, however, a hydrophilic polymeric material backbone should accelerate it. Additionally, a hydrophilic polymeric material backbone may, in some cases, increase the rate of water absorption into the material, expanding (e.g., swelling) the polymeric material and accelerating release rate. The expansion and dissolution of the material may be increased, in some embodiments, under conditions when free reactive groups contain ionizable moieties that become charged in the presence of aqueous media. In some such embodiments, as the material disintegrates due to ionic repulsion, the rate of release of contents may be increased via diffusion and/or better access to cleavable bonds may be imparted. Those skilled in the art would be capable of selecting suitable methods for determining the partition coefficient of the active substance including, for example, high performance liquid chromatography (HPLC).

The active substance may be associated with the polymeric matrix and/or present in the component in any suitable amount. In some embodiments, the active substance is present in the component in an amount ranging between about 0.01 wt % and about 50 wt % versus the total component weight. In some embodiments, the active substance is present in the component in an amount of at least about 0.01 wt %, at least about 0.05 wt %, at least about 0.1 wt %, at least about 0.5 wt %, at least about 1 wt %, at least about 2 wt %, at least about 3 wt %, at least about 5 wt %, at least about 10 wt %, at least about 20 wt %, at least about 30 wt %, at least about 40 wt % versus the total component weight. In certain embodiments, the active substance is present in the component in an amount of less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 3 wt %, less than or equal to about 2 wt %, less than or equal to about 1 wt %, less than or equal to about 0.5 wt %, less than or equal to about 0.1 wt %, or less than or equal to about 0.05 wt %. Combinations of the above-referenced ranges are also possible (e.g., between about 0.01 wt % and about 50 wt %). Other ranges are also possible.

Advantageously, the polymeric components described herein may permit higher concentrations (weight percent) of active substances such as therapeutic agents to be incorporated into the polymeric components as compared to other polymers such as hydrogels. In some embodiments, the active substance (e.g., the active substance) may be released from the component. In certain embodiments, the active substance is released by diffusion out of the component. In some embodiments, the active substance is released by degradation of the component (e.g., biodegradation, enzymatic degradation, hydrolysis). In some embodiments, the active substance is released from the component at a particular rate. Those skilled in the art would understand that the rate of release may be dependent, in some embodiments, on the solubility of the active substance in the medium in which the component is exposed, such as a physiological fluid such as gastric fluid. The ranges and description included related to the release and/or rate of release of the active substance is generally in reference to hydrophilic, hydrophobic, and/or lipophilic active substances in simulated gastric fluid (e.g., as defined in the United States Pharmacopeia (USP)). Simulated gastric fluids are known in the art and those skilled in the art would be capable of selecting suitable simulated gastric fluids based on the teachings of this specification.

In some embodiments, between 0.05 wt % to 99 wt % of the active substance is released between 24 hours and 1 year. In some embodiments, between about 0.05 wt % and about 99.0 wt % of the active substance is released from the component after a certain amount of time. In some embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the active substance associated with the component is released from the component after about after about 24 hours, after about 32 hours, after about 72 hours, after about 96 hours, or after about 192 hours. In certain embodiments, at least about 0.05 wt %, at least about 0.1 wt %, at least about 0.5 wt %, at least about 1 wt %, at least about 5 wt %, at least about 10 wt %, at least about 20 wt %, at least about 50 wt %, at least about 75 wt %, at least about 90 wt %, at least about 95 wt %, or at least about 98 wt % of the active substance associated with the polymeric component is released from the component after about 1 day, after about 5 days, after about 30 days, after about 60 days, after about 120 days, or after about 365 days. For example, in some cases, at least about 90 wt % of the active substance associated with the polymeric component is released from the component after about 120 days.

In some embodiments, the active substance is released from the component at a particular initial average rate as determined over the first 24 hours of release (e.g., release of the active substance at the desired location internally of the subject, such as an internal orifice). In certain embodiments, the active substance is released at an average rate of at least about 1%, at least about 2%, at least about 5%, least about 10%, at least about 20%, at least about 30%, least about 50%, at least about 75%, at least about 80%, at least about 90%, at least about 95%, or at least about 98% of the initial average rate over a 24 hour period after the first 24 hours of release. In some embodiments, the active substance is released at an average rate of less than or equal to about 99%, less than or equal to about 98%, less than or equal to about 95%, less than or equal to about 90%, less than or equal to about 80%, less than or equal to about 75%, less than or equal to about 50%, less than or equal to about %, less than or equal to about 30%, less than or equal to about 20%, less than or equal to about 10%, less than or equal to about 5%, or less than or equal to about 2% of the initial average rate over a 24 hour period after the first 24 hours of release. Combinations of the above referenced ranges are also possible (e.g., between about 1% and about 99%, between about 1% and about 98%, between about 2% and about 95%, between about 10% and about 30%, between about 20% and about 50%, between about 30% and about 80%, and between about 50% and about 99% over a 24 hour period). Other ranges are also possible.

The active substance may be released at an average rate over a 24 hour period of between about 1% and about 99% of the initial average release rate (measured during the first 24 hour period of release) between 48 hours and about 1 year (e.g., between 48 hours and 1 week, between 3 days and 1 month, between 1 week and 1 month, between 1 month and 6 months, between 3 months and 1 year, between 6 months and 2 years) after the initial release.

For example, in some cases, the active substance may be released at a rate of between about 1% and about 99% of the initial rate on the second day of release, the third day of release, the fourth day of release, the fifth day of release, the sixth day of release, and/or the seventh day of release.

The active substance is generally not released as a burst release from the component. In an illustrative embodiment, in which at least about 0.05 wt % of the active substance is released from the component after about 24 hours, between about 0.05 wt % and about 99 wt % is released during the first day of release (e.g., at the location internally of the subject), and between about 0.05 wt % and about 99 wt % is released during the second day of release. Those skilled in the art would understand that the active substance may be further released in similar amounts during a third day, a fourth day, a fifth day, etc. depending on the properties of the component and/or the active substance.

In certain embodiments, the active substance may be released as a pulse release. For example, in some embodiments, the active substance may be released on the first day of release and another 24 hour period such as starting during the third day, the fourth day, or the fifth day, but not released on the alternative days. Those skilled in the art would understand that other days and/or combinations of pulsing and release are also possible.

The active substance may be released at a relatively constant average rate (e.g., a substantially zero-order average release rate) over a time period of at least about 24 hours. In certain embodiments, the active substance is released at a first-order release rate (e.g., the rate of release of the active substance is generally proportional to the concentration of the active substance) of a time period of at least about 24 hours.

In some embodiments, at least a portion of the active substance loaded into the device is released continuously (e.g., at varying rates) over the residence time period.

As described herein, in some embodiments, the device is configured to adopt a shape and/or size compatible with oral administration to and/or ingestion by a subject. In some embodiments, the one or more self-assembling structures has a shape with a capacity for folding and/or packing into stable encapsulated forms. For example, in some embodiments the self-assembling structures are designed to maximally pack and fill a capsule or other soluble container (e.g., a containing structure). In some embodiments, the self-assembling structures has a shape that maximally fills and/or packs into a capsule or other soluble container. Depending on the embodiment, a capsule or other container may be configured to contain one or more self-assembling structures.

Depending on the application, a capsule may be manufactured to particular specifications or a standard size, including, but not limited to, a 000, 00, 0, 1, 2, 3, 4, and 5, as well as larger veterinary capsules Su07, 7, 10, 12e1, 11, 12, 13, 110 ml, 90 ml, and 36 ml. In some embodiments, the structure may be provided in capsules, coated or not. The capsule material may be either hard or soft, and as will be appreciated by those skilled in the art, typically comprises a tasteless, easily administered and water soluble compound such as gelatin, starch or a cellulosic material.

In other embodiments, one or more self-assembling structures are retained in a packed shape by a soluble retaining element, such as a band or surgical thread. In some embodiments, a self-assembling device comprises optimal combinations of materials with high and low elastic moduli, giving the device the capacity to alter its shape and/or size once the soluble container and/or soluble retaining element is removed.

Any terms as used herein related to shape, orientation, alignment, and/or geometric relationship of or between, for example, one or more articles, compositions, structures, materials and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elipitical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such an article to have surfaces or sides that are perfectly planar or linear and that intersect at angles of exactly 90 degrees (indeed, such an article can only exist as a mathematical abstraction), but rather, the shape of such an article should be interpreted as approximating a "square," as defined mathematically, to an extent typically achievable and achieved for the recited fabrication technique as would be understood by those skilled in the art or as specifically described.

The term "subject," as used herein, refers to an individual organism such as a human or an animal. In some embodiments, the subject is a mammal (e.g., a human, a non-human primate, or a non-human mammal), a vertebrate, a laboratory animal, a domesticated animal, an agricultural animal, or a companion animal. In some embodiments, the subject is a human. In some embodiments, the subject is a rodent, a mouse, a rat, a hamster, a rabbit, a dog, a cat, a cow, a goat, a sheep, or a pig.

The term "electrophile," as used herein, refers to a functionality which is attracted to an electron and which participates in a chemical reaction by accepting an electron pair in order to bond to a nucleophile.

The term "nucleophile" as used herein, refers to a functionality which donates an electron pair to an electrophile in order to bond to a electrophile.

As used herein, the term "react" or "reacting" refers to the formation of a bond between two or more components to produce a stable, isolable compound. For example, a first component and a second component may react to form one reaction product comprising the first component and the second component joined by a covalent bond. The term "reacting" may also include the use of solvents, catalysts, bases, ligands, or other materials which may serve to promote the occurrence of the reaction between component(s).

A "stable, isolable compound" refers to isolated reaction products and does not refer to unstable intermediates or transition states.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R"') wherein R', R", and R"' each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valencies of the heteroatoms. This disclosure is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

As used herein, the term "network" refers to a three dimensional substance having oligomeric or polymeric strands interconnected to one another by crosslinks.

As used herein, the term "strand" refers to an oligomeric or polymeric chain of one monomer unit, or an oligomeric or polymeric chain of two or more different monomer units.

As used herein, the term "backbone" refers to the atoms and bonds through which the monomer units are bound together. As used herein, the term "prepolymer" refers to oligomeric or polymeric strands which have not undergone crosslinking to form a network.

As used herein, the term "crosslink" refers to a connection between two strands. The crosslink may either be a chemical bond, a single atom, or multiple atoms. The crosslink may be formed by reaction of a pendant group in one strand with the backbone of a different strand, or by reaction of one pendant group with another pendant group. Crosslinks may exist between separate strand molecules, and may also exist between different points of the same strand.

As used herein, the term "active substance" refers to a compound or mixture of compounds which causes a change in a biological substrate. Exemplary classes of active substances in the medical and biological arts include therapeutic, prophylactic and diagnostic agents. The active substance may be a small molecule drug, a vitamin, a nutrient, a biologic drug, a vaccine, a protein, an antibody or other biological macromolecule. The active substance may be a mixture of any of the above listed types of compounds.

"Immunosuppressive agent" refers to an agent that inhibits or prevents an immune response to a foreign material in a subject. Immunosuppressive agents generally act by inhibiting T-cell activation, disrupting proliferation, or suppressing inflammation.

As used herein, the terms "oligomer" and "polymers" each refer to a compound of a repeating monomeric subunit. Generally speaking, an "oligomer" contains fewer monomeric units than a "polymer." Those of skill in the art will appreciate that whether a particular compound is designated an oligomer or polymer is dependent on both the identity of the compound and the context in which it is used.

One of ordinary skill will appreciate that many oligomeric and polymeric compounds are composed of a plurality of compounds having differing numbers of monomers. Such mixtures are often designated by the average molecular weight of the oligomeric or polymeric compounds in the mixture. As used herein, the use of the singular "compound" in reference to an oligomeric or polymeric compound includes such mixtures.

As used herein, reference to any oligomeric or polymeric material without further modifiers includes said oligomeric or polymeric material having any average molecular weight. For instance, the terms "polyethylene glycol" and "polypropylene glycol," when used without further modifiers, includes polyethylene glycols and polypropylene glycols of any average molecular weight.

As used herein, the term "Michael acceptor" refers to a functional group having a carbon-carbon double or triple bond in which at least one of the carbon atoms is further bonded to a carbonyl group or carbonyl analogs such as imine, oxime, and thiocarbonyl. The reaction between a Michael acceptor and nucleophile results in the formation of a covalent bond between the nucleophile and the carbon atom not directly connected to the carbonyl group or carbonyl analog. The reaction between a Michael acceptor and a nucleophile may be called a "Michael addition."

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkoxy" refers to an alkyl group, as defined above, having an oxygen atom attached thereto. Representative alkoxy groups include methoxy, ethoxy, propyloxy, and tert-butoxy. An "ether" is two hydrocarbons covalently linked by an oxygen.

The term "alkylthio" refers to an alkyl group, as defined above, having a sulfur atom attached thereto. In some embodiments, the "alkylthio" moiety is represented by one of S-alkyl, —S-alkenyl, and —S-alkynyl. Representative alkylthio groups include methylthio and ethylthio.

The term "amido" is art-recognized as an amino substituted by a carbonyl group.

The term "aralkyl", as used herein, refers to an alkyl group substituted with an aryl group. The term "heteroaralkyl", as used herein, refers to an alkyl group substituted with a heteroaryl group.

The term "heteroatom" as used herein means an atom of any element other than carbon or hydrogen. Examplary heteroatoms are nitrogen, oxygen, and sulfur.

As used herein, the term "thiol" means —SH; the term "hydroxyl" means —OH; and the term "sulfonyl" means —SO2-.

As used herein the term "oxo" refers to a carbonyl oxygen atom.

As used herein, the term "alkaloid" refers to a naturally occurring organic compound containing at least one non-peptidic nitrogen atom.

EXAMPLES

The following examples are intended to be illustrative in nature. Therefore, the examples should not be interpreted as exemplify the full scope of the current disclosure which should be interpreted in view of the specification and figures as a whole instead.

Example 1—Efficiency of Self-Assembled Structures

Figure 5A:
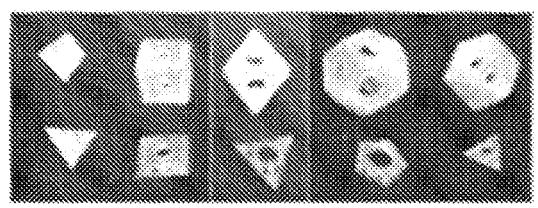
FIG. 5A is a photograph of five self-assembling structures and their corresponding aggregate structures, according to some embodiments.
Figure 5B:
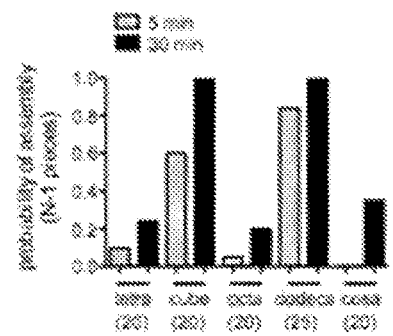
FIG. 5B is chart showing the probability of forming an aggregate structure for the five self-assembling structures of FIG. 5A.

The efficiency of self-assembly of centimeter-scale forms of different platonic solids was tested, and the results are presented in FIGS. 5A-5F. An in vitro self-assembly model was developed loosely based on the human stomach. The model consisted of a 250-ml sealed plastic container configured to be gently rotated end over end on a skewed axis at a variable rate of revolution. Polygonal self-assembling structures corresponding to each of the five platonic solids, as shown in FIG. 5A, were generated using three-dimensional printing. The circumscribing radius of each substructure was held constant at 1 cm. Neodymium magnets, with a diameter of 1/16 inch, were inserted into holes inscribed into the edges of each structure with a prescribed north-south orientation such that the substructures could interact to form a polyhedron. The effective radius, defined as the circumscribing radius R of the assembled polyhedral, is related to the specific shape of the self-assembling structures. A number of structures equal to the number of surfaces N of each of the polyhedra were assessed for efficiency of assembly by undergoing rotation in the model at 10 revolutions per minute (rpm) for up to 30 minutes. At 5 minutes, 10 minutes, 20 minutes, and 30 minutes, the largest correctly formed aggregate was identified and the number of structures (surfaces) counted. Because the final structure was frequently trapped in the interior of the assembled aggregate structure and not critical to the stability of the overall assembly, efficiency of self-assembly was calculated by determining whether N−1 structures came together correctly. The chart in FIG. 5B illustrates the probability of self-assembly for the polyhedra at 5 minutes and 30 minutes, demonstrating unexpected differences in the relatively increased self-assembly efficiency for a cube and a dodecahedron aggregate structure over a tetrahedron, octahedron, or icosahedron.

Figure 5C:
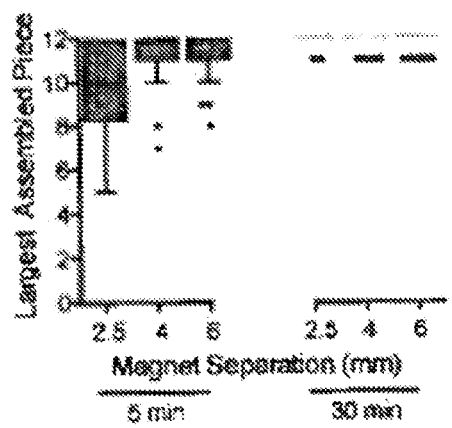
FIG. 5C is a chart showing the dependence of self-assembly efficiency versus magnet separation.

Due to its unexpected efficiency of self-assembly and larger effective size, the dodecahedron was chosen for further study. The chart in FIG. 5C illustrates the relationship between the largest assembled dodecahedron and magnet separation over time. The magnetic interaction was varied experimentally by varying the separation distance between two reversed magnets with opposite magnetic orientations (i.e. the north south axes were opposed to one another) on each edge of the substructures from 2.5 mm to 6 mm. No significant differences were found in the efficiency of assembly as measured by the largest correctly assembled structure at each time point during rotation at 10 rpm.

Figure 5D:
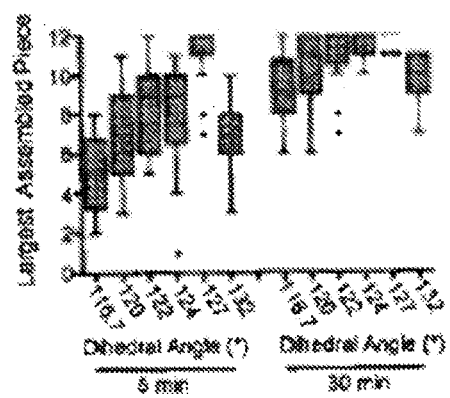
FIG. 5D is a chart showing the dependence of self-assembly efficiency versus dihedral angle.

The chart in FIG. 5D further illustrates the relationship between the largest assembled piece and the dihedral angle (i.e., the angle formed between two substructures) over time. A geometric exact fit occurs at a dihedral angle of approximately 116.6° for a dodecahedron. In these experiments, substructures providing dihedral angles ranging from 116.6° up to 132° were generated and assembly efficiency was assessed in the same fashion as described above. The chart shows that assembly efficiency varies in an approximate inverted U-curve with optimal assembly efficiency unexpectedly occurring at intermediate dihedral angles. As the dihedral angle increases from a geometric exact fit, assembly efficiency increases until the dihedral angle is increased to between about 127° and 132°; at that point self-assembly efficiency begins to decline as the degree of misalignment becomes too great for complete assembly to occur.

Figure 5E:
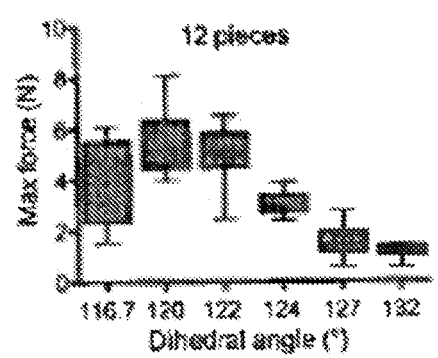
FIG. 5E is a chart showing the dependence of compressive strength versus dihedral angle.
Figure 5F:
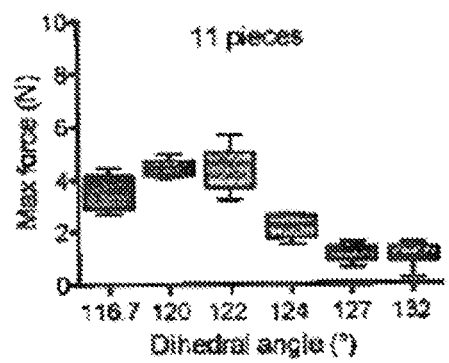
FIG. 5F is a chart showing the dependence of compressive strength versus dihedral angle.

To assess the stability of dodecahedra with dihedral angles deviating from the exact geometric fit, compression analyses were performed to find the maximum force required to compress a fully formed dodecahedron. The chart in FIG. 5E illustrates the relationship between the maximum force and dihedral angle for a dodecahedron including 12 pieces (self-assembling structures). The maximum force declines significantly at dihedral angles greater than about 124°. The same analysis was performed on incompletely assembled dodecahedra with only 11 pieces (self-assembling structures) since that structure was observed frequently. The missing structure (surface) of the dodecahedra was oriented away from the axis of compression. The chart in FIG. 5F illustrates the relationship between the maximum force and dihedral angle for 11 pieces. A similar pattern of variation with dihedral angle was found with slightly reduced compression pressures required. The maximum force required to compress a dodecahedral structure with a surface area of approximately 0.5 cm$^2$ was approximately 5 N for each configuration, which is comparable to estimates of the maximum pressure exerted at the human gastro-esophageal sphincter.

Figure 6A:
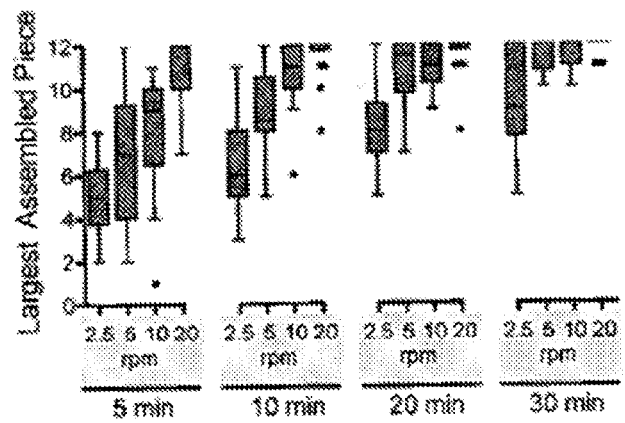
FIG. 6A is a chart showing the dependence of self-assembly efficiency versus mixing speed.
Figure 6B:
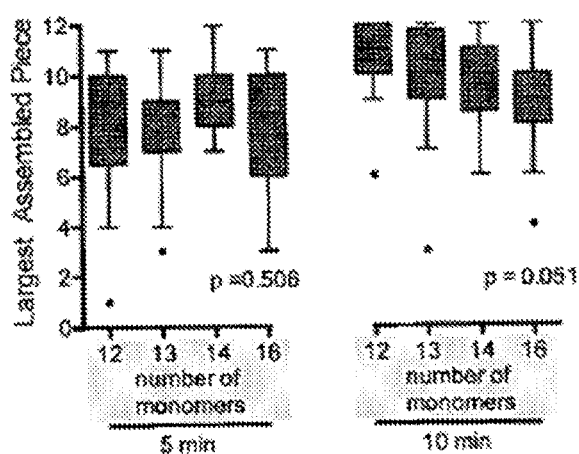
FIG. 6B is a chart showing the dependence of self-assembly efficiency versus the number of self-assembling structures.

The robustness of dodecahedral assemblies under varying conditions was assessed using the above described model, and the results are presented in FIG. 6. Assembly efficiency is known to vary with the kinetic energy applied to the system. As the rate of rotation of the container was varied from 2.5 rpm to 40 rpm, the average time required for assembly to occur, as well as the overall efficiency of assembly, increased with the rate of rotation as shown in FIG. 6A. At rotation speeds greater than 5 rpm, self-assembly was efficient, reaching 11 or 12 self-assembling structures correctly assembled in greater than 85% of cases. As shown FIG. 6B, the addition of an excess of substructures, for example, 12, 13, 14, and 16 substructures, at a rotation rate of 10 rpm, did not reduce rate of assembly by a statistically significant amount. However, a weak trend suggested excess substructures may be at least slightly unfavorable.

Figure 6C:
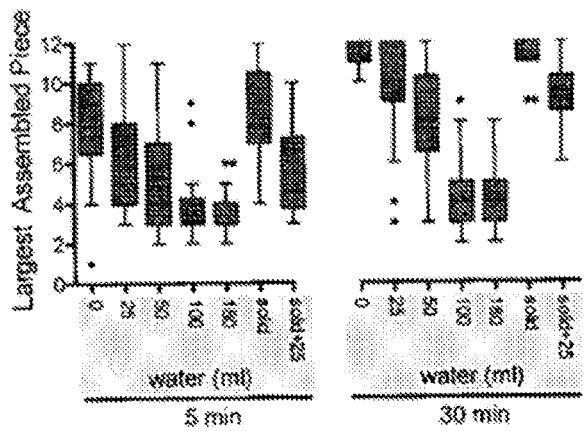
FIG. 6C is a chart showing the effect of water versus the self-assembly efficiency.

The influence of varying amounts of water in the 250 ml container on dodecahedral assembly was also assessed. As shown in FIG. 6C, water in excess of 25 ml appeared to reduce the efficiency of self-assembly of the dodecahedron by a statistically significant amount. A 1 cm diameter rubber ball was added to the container to simulate a solid food bolus in the stomach, and no effect on the efficiency of assembly was observed.

Furthermore, the addition of a rubber ball was not able to rescue the deleterious effect of more than 25 ml of water.

Example 2—In Vivo Evaluation of Self-Assembly

Figure 7:
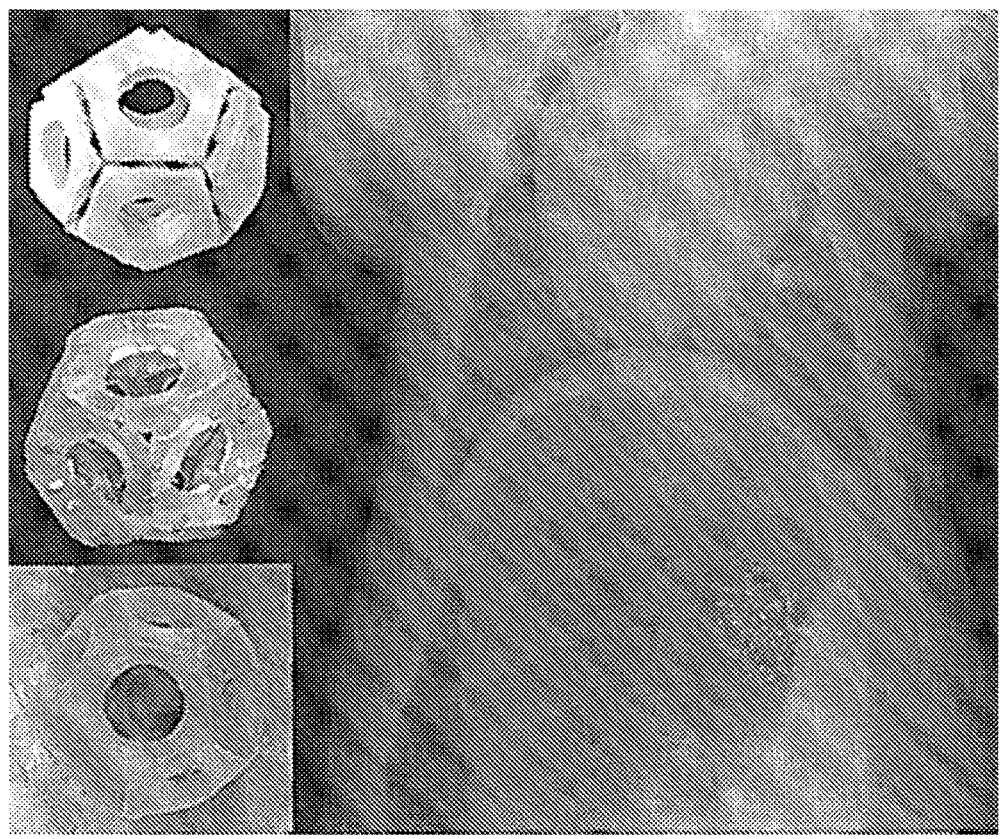
FIG. 7 shows one embodiment of a self-assembled aggregate structure retained in a gastric cavity.

FIG. 7 shows an embodiment of a self-assembled dodecahedral aggregate structure maintained in the stomach of a 55-kg pig. The pentagonal structures were placed via gastric lavage into the stomach. Within minutes, the substructures had interacted to form a semi-ordered aggregate in vivo. The dodecahedral aggregate structure was retained for 24 hours, limited by only the degradation rate of the constituent PEG-based material.

Example 3—Semi-Ordered Aggregate Structures

Figure 8A:
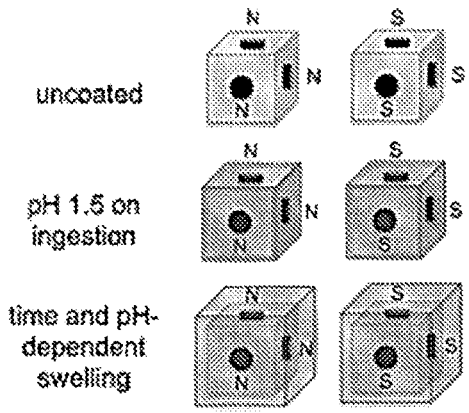
FIG. 8A is a schematic representation of one embodiment of self-assembling structures configured to form a semi-ordered aggregate structure and swell in an acidic environment.

FIG. 8A shows a schematic representation of cubic self-assembling structures which may be used to form a semi-ordered aggregate structure. As shown in the figure, the cubes include magnets with alternating magnetic orientations configured such that the cubes assemble into a semi-ordered aggregate structure. The cubes also include a coating adapted to swell over time in an acidic environment. The swelling pushes apart the cubes over time to facilitate degradation of the magnetic attachment.

Figure 8B:
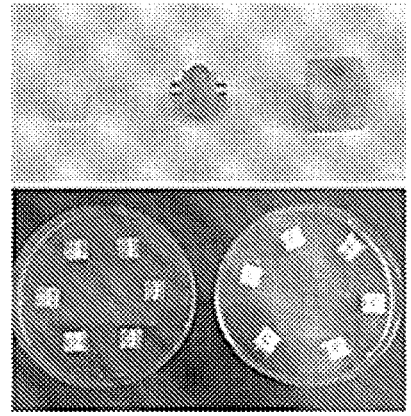
FIG. 8B shows photographs of self-assembling structures corresponding to the embodiment of FIG. 8A.
Figure 8C:
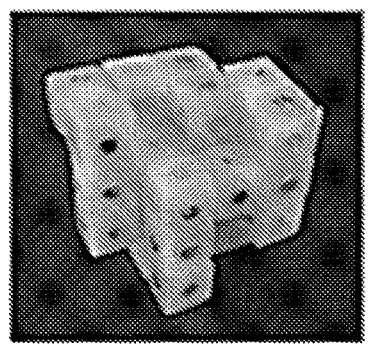
FIG. 8C is a photograph of a semi-ordered aggregate structure formed with self-assembling structures corresponding to the embodiment of FIG. 8A.

As depicted in FIG. 8B, the self-assembling cubes can be formed by inserting the magnets in a structure arranged to hold the magnets such that the magnets are arranged along the six directions corresponding to the cubic structure. Additional material is added to form a cubic shape with the magnets flush with the surface of the cube surfaces. FIG. 8C shows an exemplary self-assembled aggregate structure.

Figure 8D:
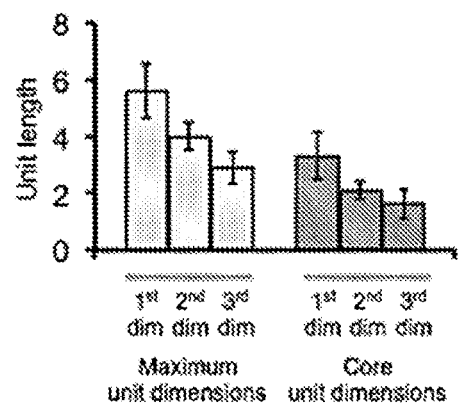
FIG. 8D is a chart depicting the size of formed semi-ordered aggregate structures.

The assembly of the cubic structures was assessed by placing 27 self-assembling cubic structures prepared by three dimensional printing in a dry mixer and rotating the mixer for 5 minutes. The maximum number of cubes along each of the three orthogonal directions corresponding to the cube structure was measured; the results are shown in FIG. 8D. In addition to the maximum dimension, a core dimension was measured, which reflects the largest fully formed cubic structure without any missing units which was contained within the observed structure.

Example 4—Gastric Retention of Semi Ordered Structures

Figure 9A:
FIG. 9A shows a semi-ordered structure retained in a gastric cavity at day 0.
Figure 9B:
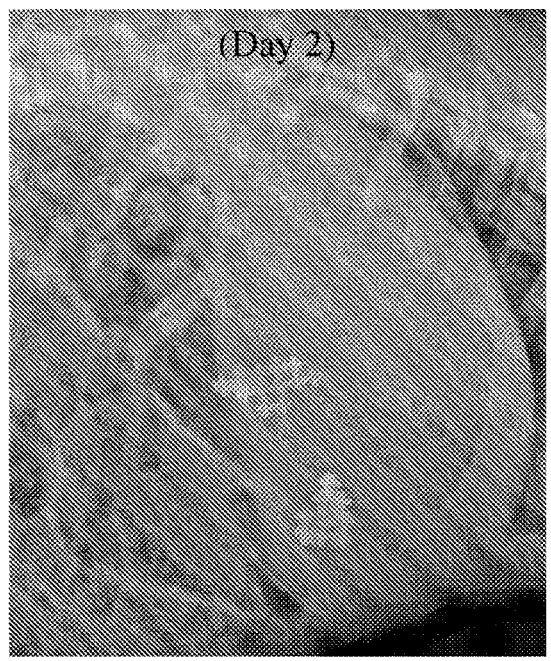
FIG. 9B shows the semi-ordered structure of FIG. 9A after 2 days after it has begun to disassociate.

FIG. 9A shows a semi-ordered aggregate structure that was formed in a Yorkshire pig after ingesting multiple self-assembling structures at day 0 after the self-assembly process has occurred. The aggregate structure is large enough to maintain a position of the aggregate structure within the gastric cavity. After two days, as shown in FIG. 9B, the attachments between the separate self-assembly structures has begun to degrade. Correspondingly, the semi ordered aggregate structure has broken apart into two smaller fragments/aggregate structures. However, the resulting fragments are still large enough to be retained in the gastric cavity. While not illustrated in the figures, this degradation process will continue until the resulting fragments of the aggregate structure are small enough to pass through an orifice out of the gastric cavity.

FIGS. 10A-10E show images from a necropsy that was performed two days following administration of a plurality of self-assembling cubic structures to a Yorkshire pig. FIGS. 10A-10B depict a semi-ordered aggregate structure confirmed to be retained in the gastric cavity. FIGS. 10C-10D show two semi-ordered aggregate structures removed from the gastric cavity during the necropsy.

Example 5—In Vivo Assembly of Semi-Ordered Structures

Figure 11A:
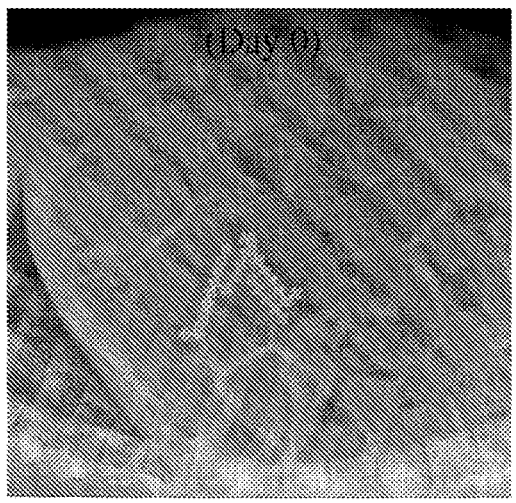
FIG. 11A shows a semi-ordered structure retained in a gastric cavity at day 0 as it is beginning to form an aggregate structure.
Figure 11B:
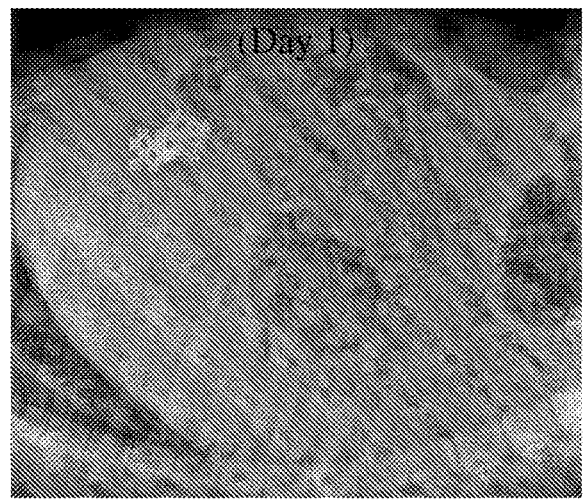
FIG. 11B shows a semi-ordered structure retained in a gastric cavity after one day.

FIG. 11A shows a plurality of self-assembling cubic structures ingested into a Yorkshire pig stomach at day 0. The self assembling cubic structures were formed as previously described with by placing neodymium magnets in an interior three dimensional structure designed to hold the magnets in place, and forming and embedding structure surrounding the magnet holder consisting of polycaprolactone mixed with crystalline powder doxycycline hyclate. Doxycycline was loaded at 20% w/w along with Pluronic P407 at 4% w/w in 76% w/w polycaprolactone (MW 45,000) through melting and mechanically mixing. The molten mixture was placed in a PDMS mold into which the magnet holder was embedded such that the magnets were exposed. As illustrated in the figure, the self-assembling structures within less than 20 minutes have formed a semi-ordered aggregate structure formed in vivo from the plurality of self-assembling. As shown in FIG. 11B, after one day, the aggregate structure has become more dense and formed a more uniform shape.

Figure 11C:
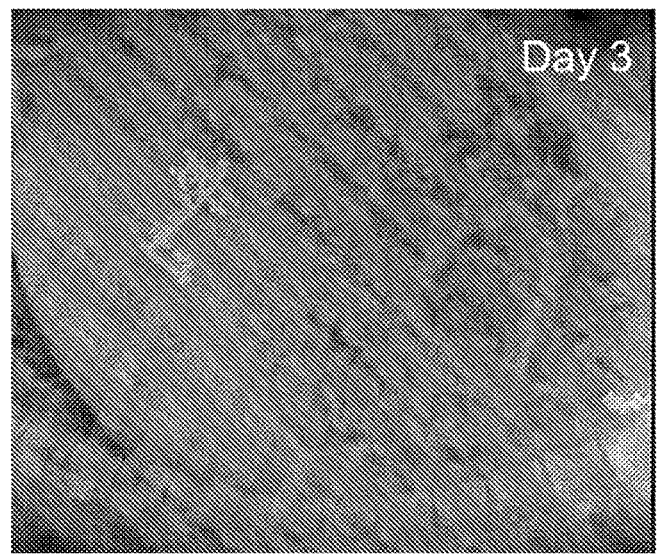
FIG. 11C shows a semi-ordered structure retained in a gastric cavity after three days.
Figure 12:
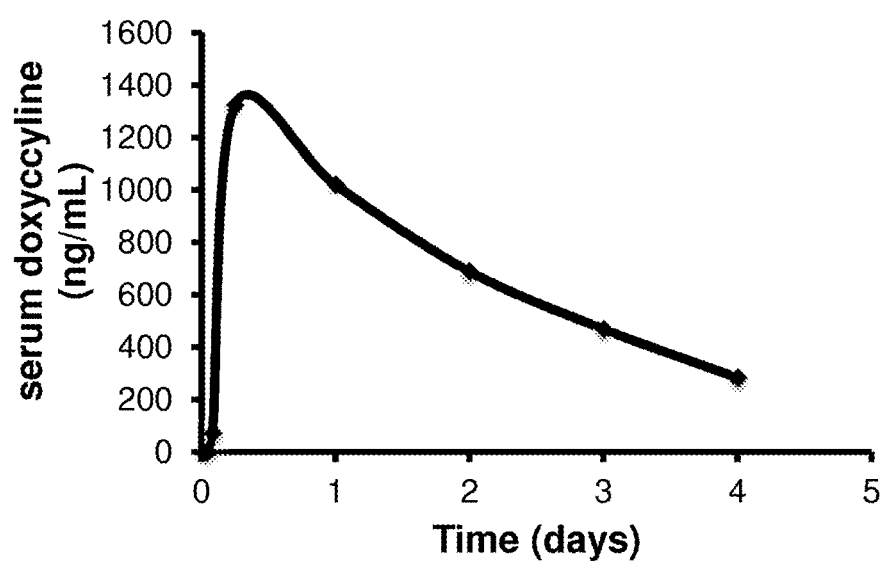
FIG. 12 shows levels of doxycycline measured in serum obtained at the indicated time points from venous cannulation of the pig before and after administering the self-assembling cubes described in FIGS. 11A-11C.

FIG. 12 shows levels of doxycycline measured in serum obtained at the indicated time points from venous cannulation of the pig before and after administering the self-assembling cubes described in FIGS. 11A-11C. Serum was analyzed by LC/LC-MS to determine concentration of doxycycline.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A residence device comprising:
 a plurality of separate self-assembling structures, each structure of the plurality of structures comprising:
 a first side; and
 a first attachment point on the first side, wherein the first attachment point is configured to attach in vivo to a second attachment point on another structure of the plurality of structures,
 wherein the plurality of structures are sized and shaped to form an aggregate structure that is sized and shaped to maintain an in vivo position relative to an internal orifice,
 wherein at least some of the plurality of self-assembling structures comprise a through hole, wherein each through hole extends from a first side of an associated self-assembling structure to a second opposing side of the associated self-assembling structure and is sized and shaped to permit passage of ingestible materials through the aggregate structure,
 wherein the internal orifice is a gastric pyloric orifice, and
 wherein an attachment between the first attachment point and the second attachment point is configured to degrade after a period of time when the plurality of structures are placed in vivo such that at least a portion of the residence device is capable of passing through the internal orifice.

2. The residence device of claim 1, wherein degradation of the attachment is caused by at least one of biodegradation of the attachment and/or swelling of at least one structure of the plurality of structures.

3. The residence device of claim 1, wherein at least one structure of the plurality of structures comprises at least one active substance.

4. The residence device of claim 3, wherein the at least one active substance includes a therapeutic agent, a diagnostic agent, and/or an enhancement agent.

5. The residence device of claim 1, wherein each structure of the plurality of structures comprises at least one of polycaprolactone, poly(ethylene-co-vinyl acetate), polyethylene glycol, a food grade cross-linked polymer, and/or an enteric elastomer.

6. The residence device of claim 1, wherein the first and second attachment points include at least one of magnets, protein-ligand complexes, and/or host-guest complexes.

7. The residence device of claim 6, wherein a protein-ligand complex comprises biotin and streptavidin.

8. The residence device of claim 6, wherein a host-guest complex comprises cyclodextrin and adamantane.

9. The residence device of claim 1, wherein each structure of the plurality of structures further comprises an exterior surface having a polygonal shape.

10. The residence device of claim 9, wherein the polygonal shape is at least one of a triangle, a square, a rectangle, and/or a pentagon.

11. The residence device of claim 1, wherein each structure of the plurality of structures further comprises an interior surface and an exterior surface opposite the interior surface, and,
 wherein the first side extends between the interior surface and the exterior surface, and wherein the first side is oriented at an angle between about 58.3° and about 66° with respect to the exterior surface.

12. The residence device of claim 11, wherein the first side is oriented at an angle between about 62° and about 63.5° with respect to the exterior surface.

13. The residence device of claim 1, wherein each structure of the plurality of structures has a circumscribing radius of about 0.6 cm to about 1.7 cm.

14. The residence device of claim 1, wherein each structure of the plurality of structures occupies a volume of about 300 mm$^3$ to about 1300 mm$^3$.

15. The residence device of claim 1, wherein each structure of the plurality of structures is configured to be at least one of ingested and/or administered orally.

16. The residence device of claim 1, wherein the aggregate structure includes a void space within an interior of the aggregate structure.

17. The residence device of claim 16, wherein the through holes are configured to provide fluid communication between the void space and an exterior of the aggregate structure.

18. The residence device of claim 3, wherein the at least one active substance includes a plurality of active substances.

19. The residence device of claim 3, wherein the at least one active substance is a biological macromolecule, a small molecule, a vitamin, and/or a supplement.

20. The residence device of claim 3, wherein the at least one active substance is at least one selected from the group of prednisone, risperidone, memantine, methadone, rosuvastatin, doxycycline, buprenorphine, aripiprazole, meloxicam, and/or azithromycin.

21. The residence device of claim 3, wherein the at least one active substance is at least one selected from the group of analgesics, anti-analgesics, anti-inflammatory drugs, antipyretics, antidepressants, antiepileptics, antipsychotic agents, neuroprotective agents, anti-proliferatives, anti-cancer agents, antihistamines, antimigraine drugs, hormones, prostaglandins, antimicrobials, antibiotics, antifungals, antivirals, antiparasitics, antimuscarinics, anxioltyics, bacteriostatics, immunosuppres sant agents, sedatives, hypnotics, antipsychotics, bronchodilators, anti-asthma drugs, cardiovascular drugs, anesthetics, anticoagulants, inhibitors of an enzyme, steroidal agents, nonsteroidal antiinflammatory agents, steroidal anti-inflammatory agents, corticosteroids, dopaminergics, electrolytes, gastro-intestinal drugs, muscle relaxants, parasympathomimetics, stimulants, anorectics, anti-narcoleptics, proteins, peptides, nucleic acids, gene constructs, rosuvastatin, selective serotonin reuptake inhibitors, blood thinning agents, steroids, F, antagonists, cardiac glycosides, alpha blockers, cholesterol absorption inhibitors, metabolites, opioids, proton-pump inhibitors, anti-malarial agents, quinine, lumefantrine, chloroquine, amodiaquine, pyrimethamine, proguanil, chlorproguanil-dapsone, a sulfonamide, mefloquine, atovaquone, primaquine, halofantrine, doxycycline, clindamycin, artemisinin, artemisinin derivatives, prednisone, risperidone, memantine, methadone, buprenorphine, aripiprazole, meloxicam, azithromycin, substance abuse treatments, hormonal contraceptives, nutritional supplements, vitamin supplements, and mineral supplements.

* * * * *

UNITED STATES PATENT AND TRADEMARK OFFICE
CERTIFICATE OF CORRECTION

PATENT NO. : 10,849,853 B2
APPLICATION NO. : 15/317628
DATED : December 1, 2020
INVENTOR(S) : Andrew Bellinger et al.

Page 1 of 1

It is certified that error appears in the above-identified patent and that said Letters Patent is hereby corrected as shown below:

In the Claims

At Column 40, Claim 21, Line 40, the word "immunosuppres sant" should be corrected to read as --immunosuppressant--;

At Column 40, Claim 21, Line 42, the word "anticoagulants" should be corrected to read as --anti-coagulants--; and At Column 40, Claim 21, Line 43, the word "antiinflammatory" should be corrected to read as --anti-inflammatory--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*